(12) United States Patent
Eggeling et al.

(10) Patent No.: US 9,759,659 B2
(45) Date of Patent: Sep. 12, 2017

(54) METHOD FOR DETECTING THE IMPACTS OF INTERFERING EFFECTS ON EXPERIMENTAL DATA

(75) Inventors: Christian Eggeling, Hamburg (DE); Kaupo Palo, Harjumaa (EE); Nicolas Fay, Hamburg (DE); Maciej Hoffman-Wecker, Hamburg (DE); Pierre Ilouga, Hamburg (DE)

(73) Assignee: EVOTEC AG, Hamburg (DE)

( * ) Notice: Subject to any disclaimer, the term of this patent is extended or adjusted under 35 U.S.C. 154(b) by 129 days.

(21) Appl. No.: 13/044,787

(22) Filed: Mar. 10, 2011

(65) Prior Publication Data

US 2011/0218767 A1    Sep. 8, 2011

Related U.S. Application Data

(60) Continuation of application No. 12/656,444, filed on Jan. 29, 2010, now abandoned, which is a division of application No. 12/068,644, filed on Feb. 8, 2008, now abandoned, which is a continuation of application No. 10/378,081, filed on Mar. 4, 2003, now abandoned.

(60) Provisional application No. 60/361,288, filed on Mar. 4, 2002.

(51) Int. Cl.
*G06F 17/18* (2006.01)
*G01N 21/64* (2006.01)

(52) U.S. Cl.
CPC . *G01N 21/6445* (2013.01); *G01N 2201/1215* (2013.01)

(58) Field of Classification Search
CPC .................................................. G01N 21/6445

USPC ........ 702/19, 21, 22, 23, 26, 27, 28, 29, 30, 702/32, 35, 36, 40, 57, 81, 82, 128, 13, 7, 702/179, 180, 181, 182, 189–194; 250/305–311, 580–582, 370.01, 370.08, 250/390.07, 395, 550–552, 250/559.01–559.08; 356/36–38, 300, 356/302–303, 450, 451, 213, 218, 237.1
See application file for complete search history.

(56) References Cited

U.S. PATENT DOCUMENTS

| | | | |
|---|---|---|---|
| 5,733,721 A | 3/1998 | Hemstreet, III et al. | |
| 5,757,022 A | 5/1998 | Kobayashi et al. | |
| 6,449,584 B1 | 9/2002 | Bertrand et al. | 702/180 |
| 6,535,836 B1 | 3/2003 | Grace | 702/179 |
| 6,818,395 B1 | 11/2004 | Quake et al. | 435/6 |

FOREIGN PATENT DOCUMENTS

| | | |
|---|---|---|
| GB | 2 318 636 | 4/1998 |
| GB | 2 318 636 A | 4/1998 |
| WO | WO 01/01112 | 1/2001 |

(Continued)

OTHER PUBLICATIONS

Kask et al. "Two Dimensional Fluorescence Intensity Distribution Analysis: Theory and Applications". Biophysical Journal, 78:4 (2000), 1703-13.

(Continued)

*Primary Examiner* — Ricky Ngon
(74) *Attorney, Agent, or Firm* — Jacobson Holman PLLC

(57) ABSTRACT

A method for identifying the impact on data, such as experimental data, of interfering effects, such as unwanted auto-fluorescence, fluorescence quenching, and fluorescent-sample deterioration, whether or not the data fulfill certain criteria with respect to a threshold indicative of the interfering effects.

4 Claims, 11 Drawing Sheets

(56) References Cited

FOREIGN PATENT DOCUMENTS

Figure 1A:
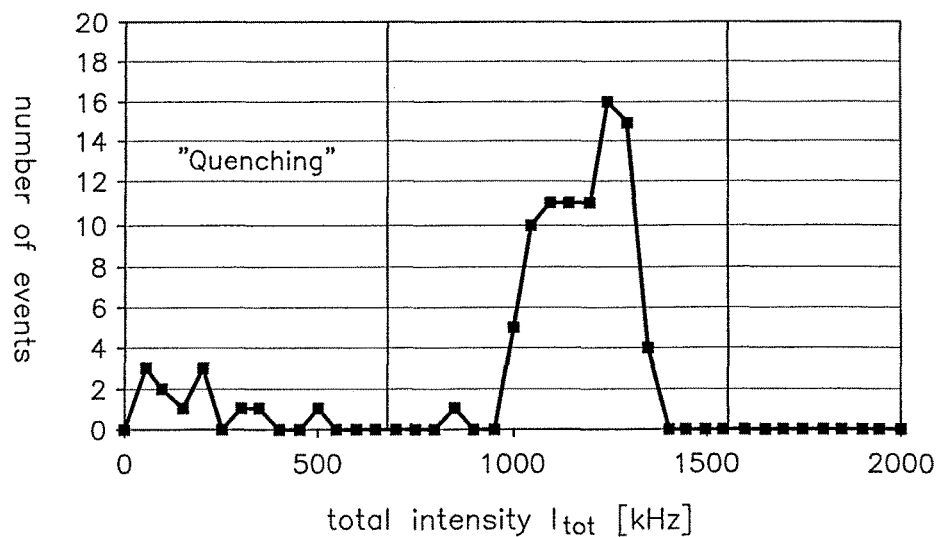

| WO | WO 01/01112 A1 | 1/2001 | ............. G01N 21/25 |
|----|----------------|--------|--------------------------|
| WO | 01/07896 A1    | 2/2001 |                          |
| WO | WO 01/07896    | 2/2001 |                          |

OTHER PUBLICATIONS

XP-002250629, 2001.
Danzer et al. "Chemometrik" 2001, Springer, XP 8.4.2.

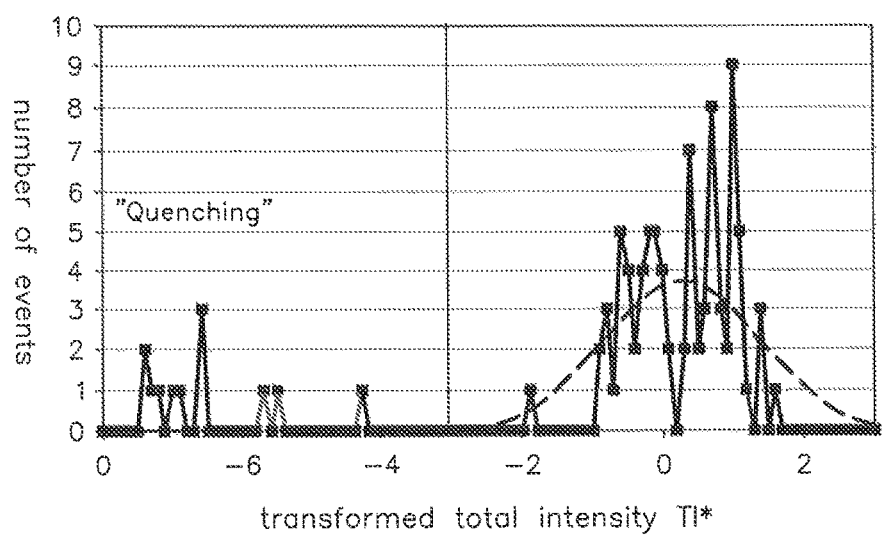
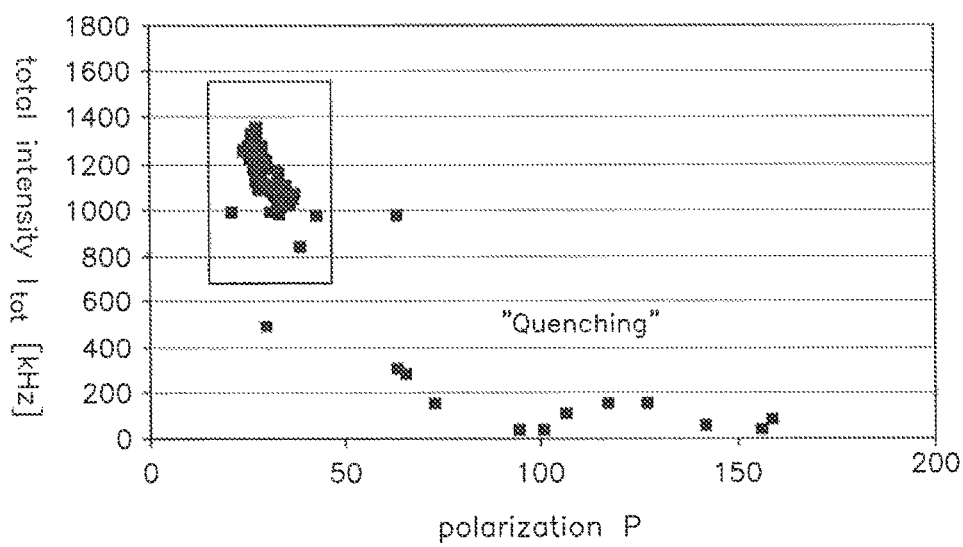

METHOD FOR DETECTING THE IMPACTS OF INTERFERING EFFECTS ON EXPERIMENTAL DATA

This is a continuation of Ser. No. 12/656,444, filed, Jan. 29, 2010, now abandoned which is a divisional of Ser. No. 12/068,644, filed, Feb. 8, 2008, now abandoned which is a continuation of Ser. No. 10/378,081, filed, Mar. 4, 2003, now abandoned which claims the benefit of U.S. Provisional Application No. 60/361,288, filed Mar. 4, 2002.

This invention relates to a method for detecting the impacts of interfering effects on experimental data such as secondary light emission data. More particularly, the invention relates to a method for detecting impacts of the effects of unwanted auto-fluorescence, of fluorescence quenching, and/or of general deterioration of the light signal on the measured data.

In the rapidly evolving field of nano-biotechnology, manipulation of particles and objects are important issues. Tools for manipulation are atomic force microscopes, magnetic tweezers, photonic force microscopes (optical tweezers), micro needles, electric fields and field cages, and levitated liquid droplets. To control these manipulation tools, secondary light emitted by the particle is often used as a feedback signal.

Apart from the manipulation of sample components, the characterization of samples plays an important role in chemistry, physics, biology, and medicine. Typical applications are chemical analysis in medicine, forensic science, material science, diagnostics, and biotechnology. Furthermore, in pre-clinical drug development, biological target molecules are examined in screening processes to identify compounds interacting with said target molecules. Very often ligand-receptor, substrate-enzyme, protein-protein, protein-DNA or protein-cell-membrane interactions are studied. Such studies are often conducted utilizing secondary light emission as a read-out. The information of emitted secondary light can e.g. be used to produce images of the sample under study. Presently, primarily fluorescence intensity is used in imaging. Further secondary light emission parameters such as fluorescence lifetime, anisotropy or polarization, or ratios of intensities from different wavelengths are also often used.

In the following, the word "light" will sometimes be used instead of "radiation". The word "light" shall not be constrained as being limited to visible radiation unless otherwise specified.

The excitation of a sample under study can e.g. take place by radiation as single-photon excitation, two-photon excitation or multi-photon excitation, or by chemical reactions. The light used for inducing a secondary light emission may be continuous or sinusoidally modulated, e.g. for phase modulation measurements, or it may be a series of light pulses. The scattering or emission of secondary light after excitation by primary light can be an elastic process, like Rayleigh-, Mie-, and Raman-scattering (e.g. Surface-Enhanced-Raman-Scattering (SERS) or Surface-Enhanced-Resonance-Raman-Scattering (SERRS)), or an inelastic process, e.g. luminescence such as phosphorescence or fluorescence. These processes are typically induced by directing electromagnetic radiation (e.g. appropriate laser light) as primary light onto the sample. Whereas elastic emission is a temporally prompt process, inelastic emission is generally delayed with respect to the excitation time. In case of luminescence, the probability of electronic deactivation and hence the inelastic emission of light is temporally exponentially distributed. The lifetime of the electronically excited state is defined as the time where the probability to be in the excited state has dropped to 1/e.

The detection of secondary emitted light can e.g. be performed on an epi-illuminated confocal fluorescence microscope using avalanche photodiodes as described in detail previously [Kask, P., Palo, K., Fay, N., Brand, L., Mets, Ü., Ullman, D., Jungmann, J., Pschorr, J. and Gall, K. (2000) Two-Dimensional Fluorescence Intensity Distribution Analysis: Theory and Applications. *Biophys. J.*, 78, 1703-1713]. Thereby, the excitation light can be in a stationary position, or be moved over and scanning the sample. Further possible set-ups are evanescent-excitation, Raman microscopes, near-field microscopes, scanning (e.g. near-field or confocal) microscopes using beam-scanners, table-scanners, and/or Nipkov-devices, as well as spectrometers using non-confocal excitation and detection. Detection might also be performed on the opposite side of the excitation. Also, the detector does not necessarily have to be an avalanche photodiode. Any sensitive detector such as photomultipliers or CCD-cameras will do.

To be detected due to emitted secondary light, the particle of interest either has to have the ability to emit light by itself or has to be labeled by a secondary light emitting tag, e.g. a fluorescent dye, a luminescent nanoparticle (e.g. a semiconductor quantum dot), or a metal chelate. In general, the particles of interest are observed in a medium such as in a solution, on surfaces, on cells, or in matrices. In drug screening processes, typically the interaction between a biological target and a luminescent ligand in the presence of low molecular weight compounds is studied. The biological target is typically involved in the pathogenesis of a disease and the compounds are screened to find possible drug candidates. In one typical experimental set-up, the influence of the compounds on the binding reaction between ligand and target is studied utilizing secondary light emission as a read-out.

There are two main disadvantages when using secondary emitted light such as fluorescence to perform characterizations of biological and/or chemical samples.

(1) "Auto-fluorescence": Background light might occur due to additional secondary light emitting particles in the sample besides the particles of interest. These particles might be the medium itself, i.e. solvent or surface molecules, impurities, and/or the added compounds. In the field of fluorescence detection, this phenomenon is known as auto-fluorescence. The auto-fluorescence interferes the detected signal which does not solely consist of actual light from the particles of interest anymore. Since the interfering auto-fluorescence has its own characteristics, the read-out (such as intensity, anisotropy, brightness, or lifetime) will be deteriorated. Let us consider the following example for illustration purposes only:

The particles of interest might emit light with intensity $I_1=120$ kHz, anisotropy $r_1=0.15$, brightness $q_1=30$ kHz, and lifetime $\tau_1=3$ ns.

The unwanted auto-fluorescence might have an intensity $I_2=80$ kHz, anisotropy $r_2=0.05$, brightness $q_2=2$ kHz, and lifetime $\tau_2=1$ ns.

Then the non-deteriorated read-out without interfering auto-fluorescence would be $I_{tot}=120$ kHz, anisotropy $r_{tot}=0.15$, brightness $q_{tot}=30$ kHz, and lifetime $r_{tot}=3$ ns.

The deteriorated read-out with interfering auto-fluorescence could be approximated via the fraction of background light, $f_2=I_2/I_{tot}=0.4$ (with $I_{tot}=I_1+I_2$), with $x_{tot}=x_1\times(1-f_2)+x_2\times f_2$ (with $x=r$, $q$, $\tau$); thus, $I_{tot}=200$ kHz, anisotropy $r_{tot}=0.11$, brightness $q_{tot}=18.8$ kHz, and lifetime $\tau_{tot}=2.2$ ns.

Samples with auto-fluorescence will therefore exhibit an increased light intensity. However, the scientist might not know that the secondary light contains spurious elements due to auto-fluorescence. The correct characterization of the particles of interest via the characteristics of the emitted light will be deteriorated and will fail.

(2) "Quenching": In the case of tagged particles, the added compounds might directly react with the secondary light emitting tag and not with the tagged particle itself. This reaction might lead to a change in the secondary light emission, mainly a decrease in light intensity. Possible reactions can be ground-state and excited-state complexes. In the field of fluorescence, this phenomenon is known as quenching. Thus, changes and characteristics in the secondary emitted light do not come from variations or properties of the tagged particle of interest anymore, but from the quenching reaction between compound and secondary light emitting tag. Again, let us consider an example for illustration purposes only:

Fluorescently labeled peptides might emit light with intensity $I_1=100$ kHz, anisotropy $r_1=0.08$, brightness $q_1=30$ kHz, and lifetime $\tau_1=3$ ns. Upon binding to a protein, the characteristics of the emitted light might change to $I_2=50$ kHz, anisotropy $r_2=0.20$, brightness $q_2=15$ kHz, and lifetime $\tau_2=1.5$ ns The binding might be activated by certain compounds. Thus, an activating compound could directly be observed by the characteristics of the emitted light due to the changes caused by the binding event.

However, imagine a non-activating compound which directly quenches the fluorescent tag. This compound might also induce changes in the emitted light, e.g. a decreased intensity and brightness, although no binding event occurred. From the characteristics of the read-out an alleged activation would be observed.

Samples with quenching compounds will exhibit a change in the emitted light, mainly a decreased light intensity. Again, the correct characterization of the tagged particles of interest via the characteristics of the emitted light will be deteriorated and will fail.

In addition to the above described cases of auto-fluorescence and quenching, a general deterioration of the signal might occur e.g. due to sample handling mistakes such as pipetting errors or due to bleaching effects of fluorescent dyes. A dye is bleached if the exciting light is causing an irreversible or reversible reaction. This reaction leads to a change in the light emission e.g. by a destruction of the dye. In the case of a destruction, the dye would irreversibly loose its ability to emit light.

In particular, in the field of high throughput drug screening, a deteriorated signal will have a severe impact on the further pre-clinical and clinical development. False positive compounds might be further optimized with high technical and financial efforts. False negative compounds might never become drugs because they have not been identified in the primary screening process. Of course, also in diagnostic and forensic applications interfering secondary light emission might have severe impacts on the data and therefore on the outcome of an experiment.

It is therefore an object of the present invention to improve the reliability of experimental data, in particular to improve the light emission read-out with respect to impacts of interfering effects on secondary light emission, in particular deterioration such as auto-fluorescence or quenching. This object is solved by the invention according to the independent claims. Advantageous embodiments of the invention are characterized in the dependent claims.

According to the present invention, a method is provided for identifying the impacts of interfering effects on experimental data. The method comprises the steps of:

(i) providing experimental data, (ii) determining values of one or a plurality of identification parameters from said data, (iii) creating a histogram or distribution of the values of the identification parameters, (iv) determining one or a plurality of thresholds for the values of identification parameters from said histogram or distribution, which thresholds are indicative for the interfering effects, (v) analyzing the values of one or a plurality of identification parameters whether or not these values fulfill one or a plurality of criteria with respect to the thresholds, and (vi) determining those data which are influenced and/or those data which are not affected by the interfering effects.

In another aspect according to the present invention, a method is provided for detecting the impacts of auto-fluorescence and/or fluorescence quenching on experimental data resulting from fluorescence experiments. The method comprises the steps of:

(i) providing the experimental data comprising a plurality of data sets, (ii) determining values of one or a plurality of identification parameters from said data sets, (iii) creating a histogram or distribution of the values of the identification parameters, (iv) determining one or a plurality of first thresholds for the values of identification parameters from said histogram or distribution, which first thresholds are indicative for auto-fluorescence, and/or determining one or a plurality of second thresholds for the values of identification parameters from said histogram or distribution, which second thresholds are indicative for fluorescence quenching, (v) analyzing the values of one or a plurality of identification parameters whether or not these fulfill one or a plurality of criteria with respect to the thresholds, and (vi) determining those data sets which are influenced and/or those data sets which are not affected by auto-fluorescence and/or fluorescence quenching.

In still another aspect of the present invention, a method is provided for detecting false positive and/or false negative results in experimental data. These data might result from screening of potentially pharmaceutical active compounds. The data might also e.g. result from diagnostic tests or forensic studies. The method comprises the steps of:

(i) providing the data, (ii) determining values of one or a plurality of identification parameters from said data, (iii) creating a histogram or distribution of the values of the identification parameters, (iv) determining one or a plurality of first thresholds for the values of identification parameters from said histogram or distribution, which first thresholds are indicative for a false-positive result, and/or determining one or a plurality of second thresholds for the values of identification parameters from said histogram or distribution, which second thresholds are indicative for a false-negative result, (v) analyzing the values of one or a plurality of identification parameters whether or not these fulfill one or a plurality of criteria with respect to the thresholds, and (vi) determining those data which represent a false-positive result and/or those data which represent a false-negative result.

In still another aspect, the invention provides a system for detecting the impacts of interfering effects on experimental data resulting from optical experiments. The system comprises:
(i) means for supporting one or a plurality of samples in an inspection station,
(ii) one or a plurality of photosensitive detectors which are positioned relative to the inspection station so that electromagnetic radiation emitted from the samples impinges on the detectors,
(iii) means for addressing the photosensitive detectors to generate experimental data,
(iv) means for determining values of one or a plurality of identification parameters from said data,
(v) means for storing the values in such a manner that preferably all the values which relate to any one of the samples are linked,
(vi) means for creating a histogram or distribution of the values of the identification parameters,
(vii) means for determining one or a plurality of thresholds for the values of identification parameters from said histogram or distribution, which thresholds are indicative for the interfering effects,
(viii) means for analyzing the values of one or a plurality of identification parameters whether or not these fulfill one or a plurality of criteria with respect to the thresholds, and
(ix) means for supplying as output information those data which are influenced and/or those data which are not affected by the interfering effects.

In a preferred embodiment, the identification parameter is selected from the group consisting of a fluorescence intensity, a ratio of fluorescence intensities at selected wavelengths, a ratio of fluorescence intensities at different polarization directions, a fluorescence anisotropy, a fluorescence polarization, a fluorescence lifetime, a rotational correlation time, a diffusion constant, a concentration of fluorophores, and a specific fluorescence brightness. In another preferred embodiment, a function of the aforementioned members of the group might be chosen as an identification parameter.

The most simple identification parameters are:
(a) The signal count rate, denoted intensity, I. Consequently, the experimental data can be checked whether they fulfill certain criteria as follows. The values of the identification parameter, in the present case the intensity values, can be checked with respect to one or a plurality of thresholds for the values of the intensity as an identification parameter, e.g. a pre-selected intensity value and/or intensity function.
(b) The anisotropy, r, or polarization, P. When employing two detectors which monitor different polarization directions of the emitted light, r and P can be calculated from the intensities with parallel, $I_P$, and perpendicular, $I_S$, polarization with respect to the polarization of the exciting light. Consequently, the data resulting from these optical experiments can be checked with the help of the identification parameter whether they fulfill certain criteria with respect to one or a plurality of thresholds. In the present case, these thresholds can be pre-selected anisotropy or polarization values. Anisotropy and polarization are typically defined as follows:

$$r=(I_P-I_S)/(I_P+2I_S) P=(I_P/+I_S)$$

(c) The ratio of intensities, f. When employing at least two detectors which monitor different wavelength ranges or different polarization directions of the emitted light, ratios or fractions of intensities detected on one or more detectors can be deduced. These can be checked whether they are in consistence with a threshold, such as a pre-selected value and/or function of intensity ratios.
(d) The lifetime, $\tau$. The mean excitation-to-detection delay time, i.e. the lifetime of the excited state of the secondary light emitting particle can e.g. be measured using pulsed light excitation together with time-correlated-single-photon-counting (TCSPC) or using modulated light excitation in general. The lifetime can be determined by a fit to the excitation-to-detection delay time histogram and even enables to distinguish secondary light emitting particles with different lifetimes within a mixture and to quantify them via their fractional intensities; this can preferably be done by performing a multi-component fit to the excitation-to-detection delay time histogram. Again, a check of the values of the identification parameters of the experimental data with regard to a pre-selected lifetime value and/or function can be conducted.
(e) The rotational correlation time, r. The rotational correlation time is directly linked to the rotational diffusion of the light emitting particles and is therefore a very nice tool to distinguish molecules of different rotational diffusion e.g. due to different mass. It can for example be determined using time-resolved anisotropy analysis. Time-resolved anisotropy is based on the same measurement principle as in the lifetime analysis. One can determine the rotational correlation time by globally analyzing the two excitation-to-detection delay time histograms recorded in the two different detection channels monitoring different polarization directions of the emitted light. This analysis enables to distinguish secondary light emitting particles with different lifetimes and/or rotational correlation times within a mixture and to quantify them via their fractional intensities; this can preferably be done by performing a multi-component fit to the excitation-to-detection delay time histograms. Again, a check of the values of the identification parameters of the experimental data with regard to a pre-selected lifetime and/or rotational correlation time value and/or function can be conducted.

More complex spectroscopic techniques have been developed which are based on the detection of single light emitting particles and which enable to resolve different light emitting particles within the same sample.
(a) The direct observation of signal bursts from single light emitting particles enables to qualitatively and quantitatively identify different light emitting particles in a mixture via their spectroscopic properties; e.g. such as realized in a dye mixture using the differing fluorescence properties: lifetime [Zander, C., Sauer, M., Drexhage, K. H., Ko, D. S., Schulz, A., Wolfrum, J., Brand, L., Eggeling, C. and Seidel, C. A. M. (1996) Detection and characterization of single molecules in aqueous solution. *Appl. Phys. B,* 63, 517-523], lifetime and intensity [Fries, J. R., Brand, L., Eggeling, C., Köllner, M. and Seidel, C. A. M. (1998) Quantitative identification of different single-molecules by selective time-resolved confocal fluorescence spectroscopy. *J. Phys. Chem. A,* 102, 6601-6613], and anisotropy [Schaffer, J., Volkmer, A., Eggeling, C., Subramaniam, V., Striker, G. and Seidel, C. A. M. (1999) Identification of single molecules in aqueous solution by time-resolved fluorescence anisotropy. *J. Phys. Chem. A,* 103, 331-336]. Accordingly, a suitable identification parameter as well as its value being indicative for a certain effect is chosen. The experimental data can be checked with the help of one or a plurality of corresponding identification parameters (e.g. lifetime; lifetime and intensity; anisotropy) for fulfilling certain criteria with respect to one or a plurality of thresholds, such as a pre-selected value of lifetime.

(b) FCS (fluorescence correlation spectroscopy) analyses the temporal characteristics of signal fluctuations from single light emitting particles. The calculated correlation function of these fluctuations decays with time constants that are characteristic of the molecular processes causing these signal changes, e.g. diffusion into and out of the detection volume and reaction kinetics. The amplitude of the decay is related to the molecular concentration while the inflection point of the correlation function represents the mean diffusion time, $\tau_{diff}$, of the fluorescing molecules through the detection volume, which is dependent on the diffusion coefficient. Hence, by a fit to the correlation function, FCS is able to resolve components of a sample with different diffusion coefficients due to their different molecular masses; in practice, preferably a multi-component fit to the correlation function is performed. Accordingly, when studying FCS data, a suitable identification parameter is the diffusion coefficient.

(c) FIDA or 1D-FIDA (fluorescence intensity distribution analysis) relies on a collection of instantaneous values of the fluctuating intensity by building up a frequency histogram of the signal amplitudes throughout a measurement [Kask, P., Palo, K., Ullman, D. and Gall, K. (1999) Fluorescence-intensity distribution analysis and its application in biomolecular detection technology. *Proc. Natl. Acad. Sci. U.S.A.*, 96, 13756-13761]. The resulting distribution of signal intensities is then analyzed by a theory which relates specific fluorescence brightness q (intensity per molecule in kHz), and absolute concentration c (mean number of molecules in the detection volume) of the molecules under investigation. By performing a fit to the frequency histogram, FIDA distinguishes species of the sample according to their different values of specific molecular brightness q; in practice, preferably a multi-component fit is performed. Consequently, when studying data collected by FIDA experiments, a suitable identification parameter is the specific molecular brightness q.

(d) Further methods such as 2D-FIDA (two-dimensional fluorescence intensity distribution analysis), FIMDA (fluorescence intensity multiple distribution analysis), or FILDA (fluorescence intensity and lifetime distribution analysis) might be applied resulting in improved performance compared to the FIDA technique.

2D-FIDA typically makes use of a two-detector set-up monitoring either different polarization or emission bands of the signal. In addition to the FIDA performance, 2D-FIDA achieves additional molecular resolution by performing a multi-component fit to the two-dimensional frequency histogram of the concurrent signal amplitudes from both detectors and, thus, the concurrent determination of two specific brightness values of each detection channel, $q_1$(channel1) and $q_2$(channel2), for each component [Kask, P., Palo, K., Fay, N., Brand, L., Mets, Ü., Ullman, D., Jungmann, J., Pschorr, J. and Gall, K. (2000) Two-Dimensional Fluorescence Intensity Distribution Analysis: Theory and Applications. *Biophys. J.*, 78, 1703-1713]. By observing the molecular resolved anisotropy, simple and more complex binding events and enzymatic reactions may be followed. Alternatively, such events may be followed using light emitting particles with different emission bands and combining this with either two-color excitation by different lasers or energy-transfer interaction. Thus, the use of a second detector can improve the power of FIDA to distinguish between molecular components and is, therefore, increasingly applied in high-performance drug discovery. When analyzing data collected by 2D-FIDA experiments, one will preferably choose two identification parameters: (i) a molecular brightness, $q_1$, at a first wavelength and/or a molecular brightness, $q_2$, at a second wavelength; alternatively (ii) a molecular brightness, $q_1$, at a first polarization and/or a molecular brightness, $q_2$, at a second polarization.

FIMDA typically only demands one detection channel and extracts all characteristics of both FCS and FIDA, i.e. diffusion time, $\tau_{diff}$, specific molecular brightness, q, and absolute concentration, c, from a single measurement [Palo, K., Mets, Ü., Jäger, S., Kask, P. and Gall, K. (2000) Fluorescence Intensity Multiple Distribution Analysis: Concurrent Determination of Diffusion Times and Molecular Brightness. *Biophys. J.* 79]. This is achieved by fitting a series of different FIDA histograms obtained from the same measurement regarding different components. FIMDA increases the readout and improves likelihood of molecular resolution of different components of the sample effectively by one dimension. Therefore, when analyzing data collected by a FIMDA experiment, one will typically choose as identification parameters a specific molecular brightness and/or a diffusion time.

FILDA as well typically only demands one detection channel and extracts all characteristics of both FIDA and lifetime determination, i.e. specific molecular brightness, q, lifetime, $\tau$, and absolute concentration, c, from a single measurement. FILDA is based on fitting a two-dimensional histogram of the number of photons detected in counting time intervals of given width and the sum of excitation-to-detection delay times of these photons, once again regarding and quantifying different fluorescent components. The combined information yielded by FILDA results in significantly increased accuracy compared to that of FIDA and lifetime analysis alone. Consequently, when analyzing FILDA data, one may choose as identification parameters a lifetime and/or a specific molecular brightness.

In all of the above methods, which can quantify each component by its concentration, c, or an according amplitude, the concentration or amplitude can as well be taken as an identification parameter.

With regard to optical experiments, the most simple identification parameter for auto-fluorescence, fluorescence quenching, and/or other general deterioration of the measured data (e.g. through measuring errors, dispensing or pipetting errors, etc) is the light intensity, since these sorts of deterioration lead to a change of the experimentally determined intensity; in principle, an increase is assumed in the case of auto-fluorescence and a decrease in the case of fluorescence quenching.

However, since auto-fluorescence and quenching change the whole characteristic of the emitted and, thus, detected light, other read-out parameters can as well be used for identification. These are for example anisotropy (r), polarization (P), ratio of intensities (f), lifetime ($\tau$), rotational correlation time ($\rho$), brightness (q), concentration (c), brightness values of different detection channels ($q_1$ and $q_2$), diffusion time ($\tau_{diff}$), or other parameters resulting from a fit to the lifetime histogram, correlation function (FCS), FIDA-, or other histogram techniques (e.g. 2D-FIDA, FIMDA, or FILDA).

The identification parameter can preferably be a quality parameter of such a fit such as a chi²-value, which is for example calculated from $$chi^2 = \sum_x W(x)[\hat{P}(x) - P(x)]^2$$

(where the sum is performed over all data points x, $\hat{P}(x)$ is the measured data, P(x) the theoretical data, and W(x) are the weights, e.g. expressed as W(x)=M/P(x) with the total number of data points, M).

Further possible identification parameters result from a moment-analysis to the lifetime histogram, correlation function (FCS), FIDA-, 2D-FIDA-, FIMDA-, or FILDA-histogram by calculating moments, correlations, cumulants, and functions of these such as
  $M_1^2/(M_2-M_1^2)$, $(M_2-M_1)/(M_1T)$, and $K_3 \times 0.55 \times K_1/K_2^2$ with the first and second moments, $M_1$ and $M_2$, and the first, second, and third factorial cumulants, $K_1$, $K_2$, and $K_3$, resulting from a one-dimensional function such as the FIDA-histogram.
  $|K_{10}+K_{01}-(K_{20}+2K_{11}+K_{02})^2/[(K_{30}+3K_{21}+3K_{12}+K_{03})\times 0.55]|$ with the factorial cumulants, $K_{xy}$, resulting from a two-dimensional function such as the 2D-FIDA-histogram.

In the case of observing images of the sample, additional identification parameters besides the ones mentioned above might come from all kinds of pattern recognition or image analysis algorithms as well as from image moment analysis.

The values of several identification parameters can also be linked to obtain a new value of a single identification parameter. Examples are mathematical procedures such as the calculation of vector lengths or of generalized square distances.

Further identification parameters can also be obtained by relating one or more of the above parameters to their values obtained from control samples such as

[X(sample)–X(control B)]/[X(control A)–X(control B)] or

[X(control A)–X(sample)]/[X(control A)–X(control B)]

where X(sample) is the identification parameter obtained from the sample and X(control A) and X(control B) are the identification parameters obtained from the two different control samples. For example, in the case of the binding of a tagged ligand to a protein, the latter relation expresses the inhibition of the binding if the control A sample represents the complete binding event and the control B the free ligand.

Data from an experiment can be classified to have been influenced by auto-fluorescence, quenching, and/or general deterioration, if e.g. the value of at least one of the above identification parameters determined from the emitted and detected light of this sample is above or below a pre-selected threshold value. In case a set of various identification parameters is used for classification, the classification rules might be that the values of all of the identification parameters have to be above or below certain corresponding threshold values, that only the value of at least one identification parameter has to be above or below a certain corresponding threshold value, or that the set of identification parameters have to fulfill certain functions or relations between the corresponding parameters. For example, if two identification parameters, $x_1$ and $x_2$, are used, the classification rules might be (a) $[x_1 > t\_up(x_1)$ and/or $x_1 < t\_low(x_1)]$ and/or $[x_2 > t\_up(x_2)$ and/or $x_2 < t\_low(x_2)]$ with upper and lower threshold values, t_up and t_low, of $x_1$ and $x_2$, respectively.

(b) $x_2 > f_1(x_1)$ and/or $x_2 < f_2(x_1)$ where $f_1$ and $f_2$ are functions of one of the parameters such as $f_i(x_1) = a_i + m_i \times x_1$ with i=1 and 2 and constants $a_i$ and $m_i$.

The pre-selected threshold values, functions and/or relations can be determined from the values of identification parameters obtained from a whole set of observed samples. The threshold values, functions and/or relations can be determined from the one-dimensional distribution of the values of one identification parameter or from the multi-dimensional distribution of the values of a set of concurrent identification parameters as obtained from all or parts of the set of observed samples.

The values of the distribution of identification parameters as determined from the set of observed samples can also be mathematically transformed or normalized to yield special properties of the distribution such as Gaussian distributions, e.g. by calculating standardized or studentized residuals.

The set of observed samples (and consequently the gathered experimental data or data sets) can either be all or parts of the samples to be analyzed and/or all or parts of control samples. Histograms or distributions of the values of the identification parameters can therefore be created from all of the data sets, e.g. including also control samples, or only parts thereof.

The threshold values, functions and/or relations can be derived from the distribution through functions of the mean, median, moments, cumulants, standard deviation, and/or the values themselves of the distribution. A possible function would be mean±y×s or median±y×s*, where y is a constant, e.g. 3, and mean and median are the mean and median of the distribution, respectively, s is the standard deviation of the distribution, and s* represents the median like standard deviation of the distribution. s* can either be obtained by (a) cutting of x % of the edges of the distribution (i.e., disregarding the x % highest and lowest values, x is a constant and can e.g. be 1) and calculating the common standard deviation of the remaining distribution, (b) calculating the median of the absolute differences between each point and the median of the distribution and multiplying this value by 1.482, (c) fitting a theoretical distribution which is a function of s* to the experimental distribution, such as the Gaussian distribution $(G(x) = A \times \exp(-2(x-x_0)^2/(2s^{*2})))$ with an amplitude, A, and the mean, $x_0$ or (d) taking the mean of the values calculated for s, in (a), (b), and/or (c). The constant, y, can be set by hand after observation of the distribution or derived from theory. For example, if the distribution of identification parameters is Gaussian-like or has been mathematically transformed or normalized to a Gaussian-like distribution, the threshold is best set to y=3. In this case, the probability to be a valid part of the distribution is 99.8%, if the value of an identification parameter is within the threshold (95.5% for y=2 and 70.5% for y=1).

For example, if only one identification parameter is chosen for identification, the corresponding one-dimensional distribution can be built up from the values of the identification parameter obtained from several samples and be transformed to a Gaussian distribution, and the upper and lower threshold values be determined as mean+3×standard deviation and mean−3×standard deviation, respectively.

For example, if two identification parameters are chosen, one can a) build up the corresponding two-dimensional distribution from the values of the identification parameters obtained from a set of two different control samples (control A and control B),
b) determine the mean values (m(control $A,x_i$), m(control $A,x_i$)) from each set of the two control samples for each identification parameter i=1 and 2,
c) determine upper (t_up(control $A,x_i$), t_up(control $B,x_i$)) and lower threshold values (t_low(control $A,x_i$), t_low (control $B,x_i$)) from each set of the two control samples for each identification parameter i=1 and 2 (e.g. by calculating mean+3×standard deviation and mean−3× standard deviation, respectively, for each set), and
d) classify auto-fluorescence, quenching, and/or general deterioration according to the condition;

$x_2 < a_1 + m_1 \times x_1$ or
$x_2 > a_2 + m_2 \times x_1$ or
[$x_1 <$ t_low(control $A,x_1$) and $x_1 <$ t_low(control $B,x_1$)] or
[$x_1 >$ t_up(control $A,x_1$) and $x_1 >$ t_up(control $B,x_1$)]
with
$m_1 =$ [t_low(control $A,x_2$)−t_low(control $B,x_2$)]/[m(control $A,x_2$)−m(control $A,x_2$)],
$a_1 =$ t_low(control $A,x_2$)−$m_1 \times$ m(control $A,x_2$)
$m_2 =$ [t_up(control $A,x_2$)−t_up(control $B,x_2$)]/[m(control $A,x_2$)−m(control $A,x_2$)],
$a_2 =$ t_up(control $A,x_2$)−$m_2 \times$ m(control $A,x_2$).

Preferably, one of the identification parameters should be the intensity (I) (or the intensity normalized to the intensity obtained from control samples as described above), whereby auto-fluorescence is identified by an increased intensity, whereas fluorescence quenching and/or general deterioration is identified by a decreased intensity.

The identification step can of course not only be applied to the said identification of general deterioration but in general to check the failure of any signal or analysis method such as a fit. For example, the results of any lifetime, FCS, FIDA, or further histogram-based analysis can be checked in this manner for a failure.

In summary, the identification step relating to data gathered from fluorescence measurements is preferably performed in three steps.
1. Selection of at least one appropriate identification parameter, one of which is preferably intensity (I) or normalized intensity.
2. Determination of pre-selected threshold values, functions, and/or relations from the values of said chosen parameters.
3. Identification of auto-fluorescence and/or fluorescence quenching according to conditions specified by the said threshold values, functions, and/or relations.

It is particularly preferred to conduct after the identification of data being influenced by auto-fluorescence, fluorescence quenching, and/or general deterioration, the following steps:
1. Correction of the read-out—in the case of auto-fluorescence with the goal to separate auto-fluorescence from the light emitted by the particles of interest.
2. Test-procedure to check whether the correction procedure has succeeded.

The correction step is performed for correcting the signal to typically separate interfering signal and extract only the information coherent with the light emitted from the particles of interest.

The correction step for interfering auto-fluorescence signal preferably demands a read-out which is able to distinguish secondary light emitting particles with different emission characteristics within the same sample and to quantify them using a multi-component analysis, i.e. which molecularly resolves the detected light. As mentioned above, read-out methods that are capable of this molecular resolution are e.g. the lifetime determination, FCS, FIDA, and further histogram-based methods such as time-resolved anisotropy, 2D-FIDA, FIMDA, or FILDA. These read-out methods enable to apply a multi-component fit to the functions or histograms obtained from the detected light and, thus, to resolve distinguishable light emitting particles.

Furthermore, the lifetime analysis based methods (lifetime determination and FILDA) enable to distinguish between an elastic light emission process such as scattering and an inelastic emission process such as luminescence, since the elastic emission is a temporally prompt process (lifetime $\tau=0$ ns) while the inelastic emission is generally delayed with respect to the excitation time ($\tau>0$ ns). Therefore, lifetime analysis offers the possibility to explicitly regard elastic light emitting particles.

In contrast, all brightness-based methods allow to explicitly regard light emitting particles with high concentration and very low brightness (detected counts per particle) such as scattering solvent particles, since the signal amplitudes originating from such components are simply Poissonian distributed. Such a signal shall be denoted FIDA-background later on. In general, this FIDA-background is fixed to a pre-selected value, e.g. determined from control experiments.

The correction procedure is applied by preferably adding an additional component to the fit, which accounts for the additional auto-fluorescence "component". Thus, the remaining components/light are cleared from the interfering auto-fluorescence light. According to the read-out method, this additional component might be accounted for in the fit as follows:

lifetime determination: an additional lifetime, which is either fixed to a pre-selected value or freely fitted, and/or a freely fitted amount of elastic light emitting particles.
FCS: an additional diffusion time, which is either fixed to a pre-selected value or freely fitted;
FIDA: an additional brightness, which is either fixed to a pre-selected value or freely fitted, and/or a freely fitted FIDA-background.
2D-FIDA: an additional pair of brightness values, where either both values are fixed to pre-selected values, only one value is fixed while the other is subject to fitting, or both values are subject to fitting, and/or a pair of FIDA-background values, where either both values are fixed to pre-selected values, only one value is fixed while the other is subject to fitting, or both values are subject to fitting.
histogram-based methods in general: an additional set of read-out parameters (e.g. brightness, lifetime, diffusion time, and/or FIDA-background), where either all values are fixed to pre-selected values, only at least one value is fixed while the others are subject to fitting, or all values are subject to fitting.

In general, the light emission of the auto-fluorescent particles is rather weak compared to the actual light emitting particles of interest. Therefore, their brightness can be assumed to be rather low, and, if fixed within a FIDA(-based) fit, the brightness values of the additional auto-fluorescent component can be fixed to a rather low value (e.g. >0 kHz to <10 kHz).

Furthermore, auto-fluorescent particles are very often highly concentrated within the sample (e.g., in screening and HTS applications compounds are added in μM-concentration, while the light emitting particles of interest are concentrated at least below 50 nM for FIDA-based applications). Therefore, the auto-fluorescence emission is very FIDA-background like and can be considered as FIDA-background in the fit or as an additional component with its concentration value fixed to a rather high value (c>50).

Since an additional component might deteriorate the accuracy of the results of the fit, it is very often preferable to apply this auto-fluorescence correction procedure only to those data which are identified to reveal auto-fluorescence properties. This means as a general rule that preferably a correction step is only performed on those data which have been identified as being influenced by interfering effects, such as auto-fluorescence or fluorescence quenching.

As outlined above, preferably a test procedure to check whether the correction step has succeeded is performed in the same manner as the identification step described above. Basically, failed correction procedures are identified and marked as bad data points.

In a first step, at least one parameter is chosen which identifies the failure of the correction procedure, denoted failure parameter. The potential failure parameters can be the same as previously described as identification parameters in the identification step. Preferably, at least one of the chosen failure parameters is a resulting value of the applied fit, e.g., a quality parameter such as the $chi^2$ value, the lifetime, rotational correlation time, diffusion time, a brightness value, or the concentration.

In a second step, threshold values, functions, and/or relations are specified from the said chosen failure parameters as described in detail in the identification step, i.e. by determining them from the distribution of values of failure parameters obtained from a whole set of observed samples or from subgroups thereof.

In a third step, a failure is classified according to conditions specified by the said threshold values, functions, and/or relations—a procedure that is analogue to the identification procedure. This procedure has in detail been described above.

The test procedure can of course not only be applied to the said correction procedure but in general to check the failure of any analysis method such as a fit. For example, the results of any lifetime, FCS, FIDA, or histogram-based analysis can be checked in this manner for a failure.

Other objects, advantages, and novel features of the invention will become apparent from the following detailed description of the invention when taken in conjunction with the accompanying drawings.

FIGS. 1A-F illustrates impacts of the effect of quenching compounds on fluorescence emission data and presents different identification methods.

FIGS. 2A-E illustrates impacts of the effect of auto-fluorescent compounds on fluorescence emission data using polarization and 2D-FIDA read-outs and presents different identification methods, a correction procedure, and a procedure for checking possible failures of the correction step.

Figure 3A:
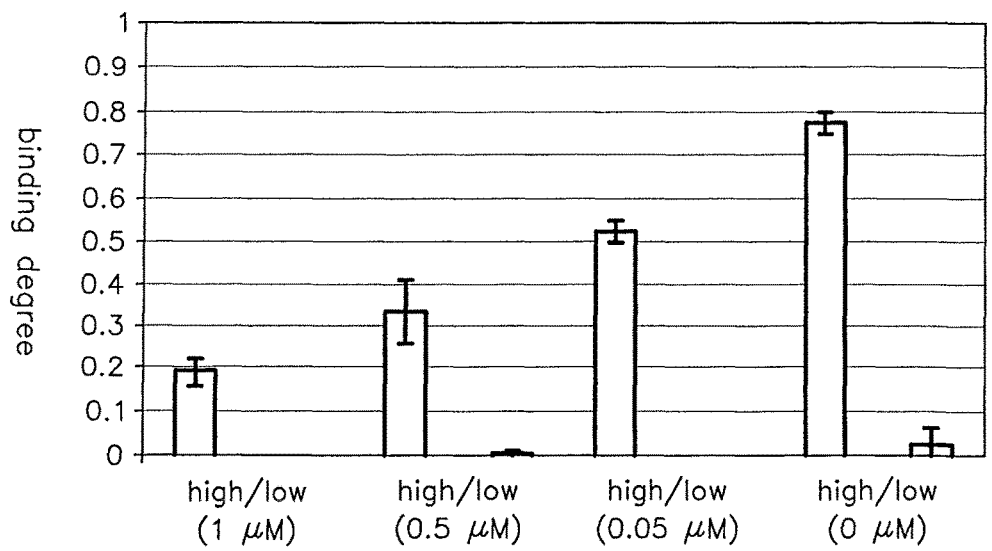
Figure 3B:
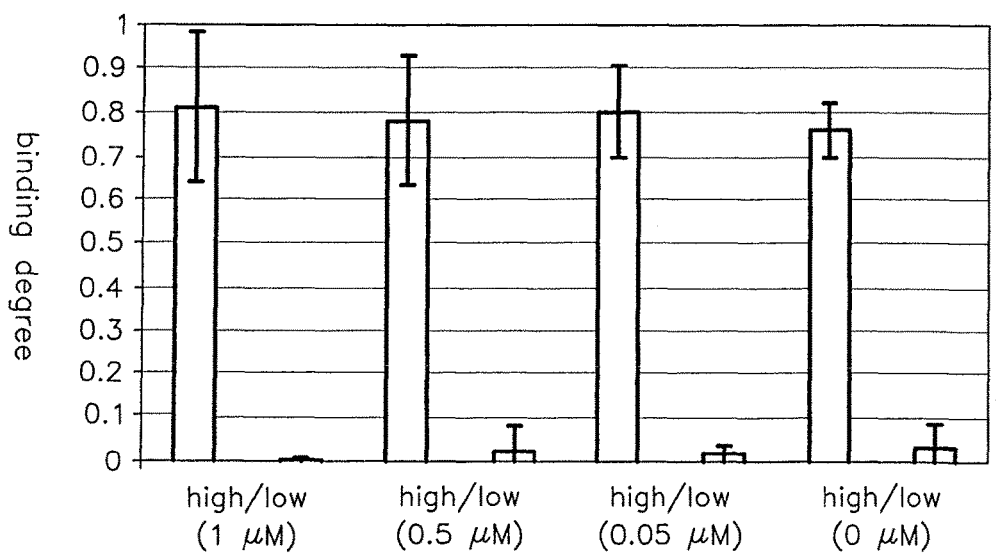

FIGS. 3A-B illustrates impacts of the effect of auto-fluorescent compounds on fluorescence emission data using FIDA read-outs and presents a correction procedure.

Figure 4A:
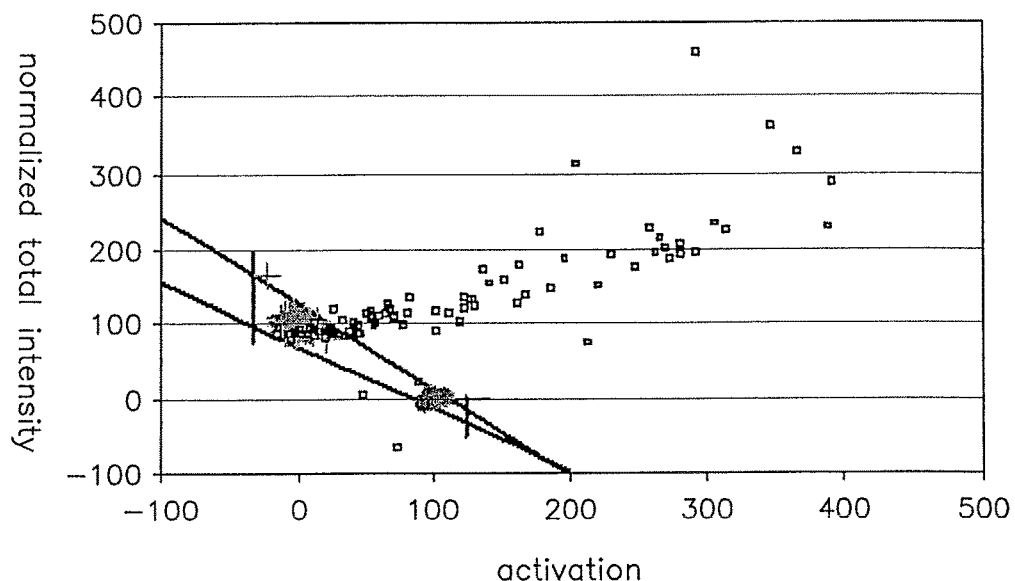
Figure 4B:
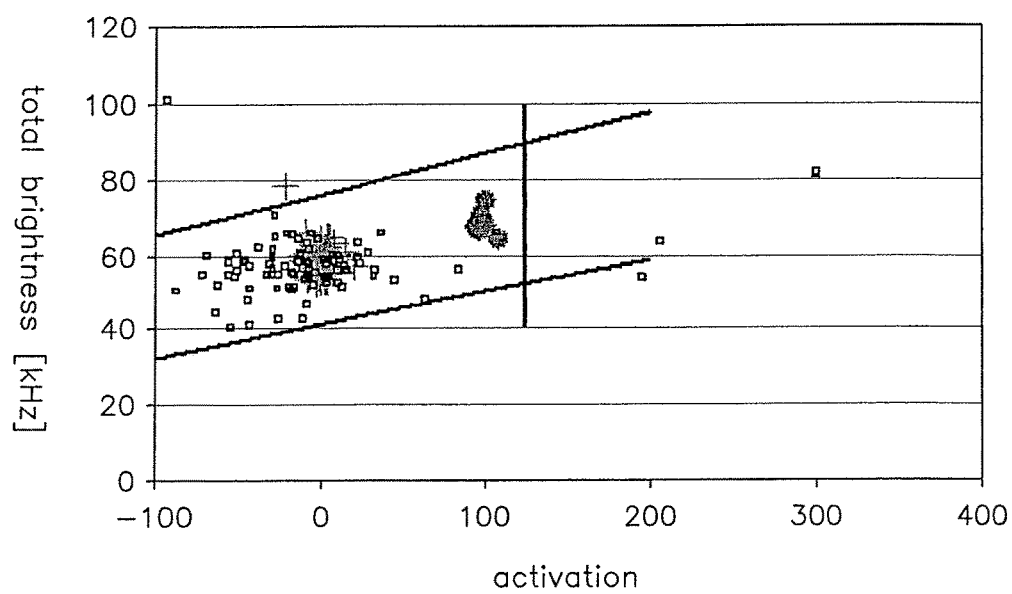

FIGS. 4A-B illustrates screening for activating compounds using polarization and 2D-FIDA read-outs and the identification of auto-fluorescent and quenching compounds, a correction procedure, and a check of the correction step in the case of auto-fluorescence.

Figure 5A:
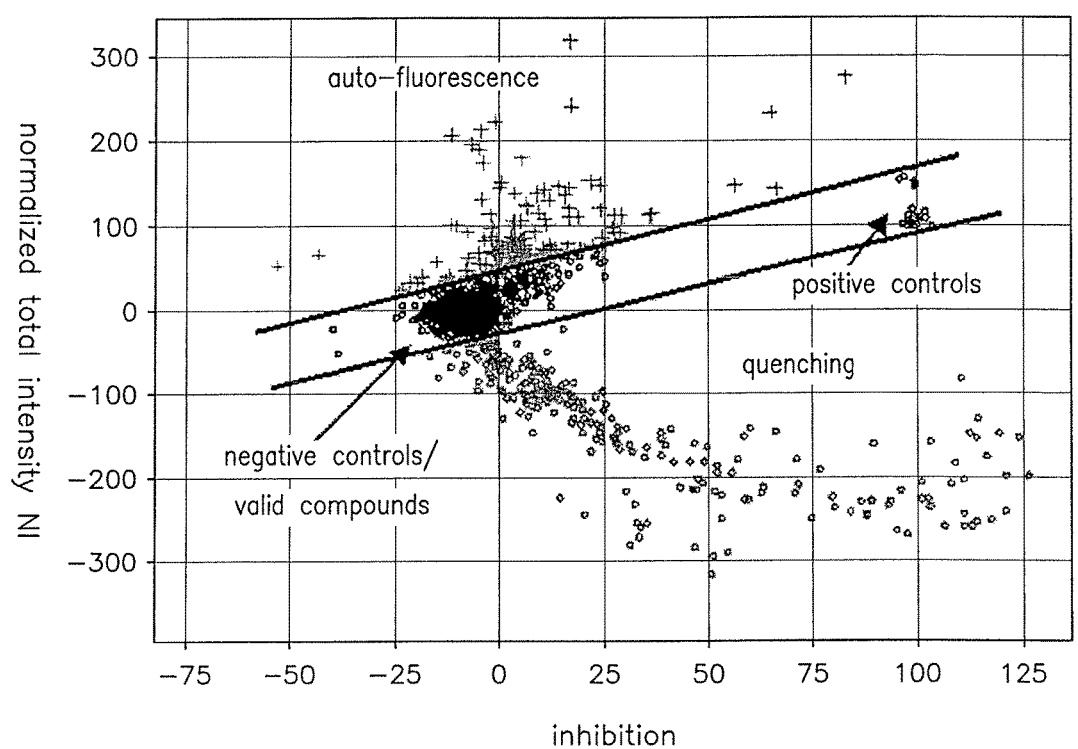
Figure 5B:
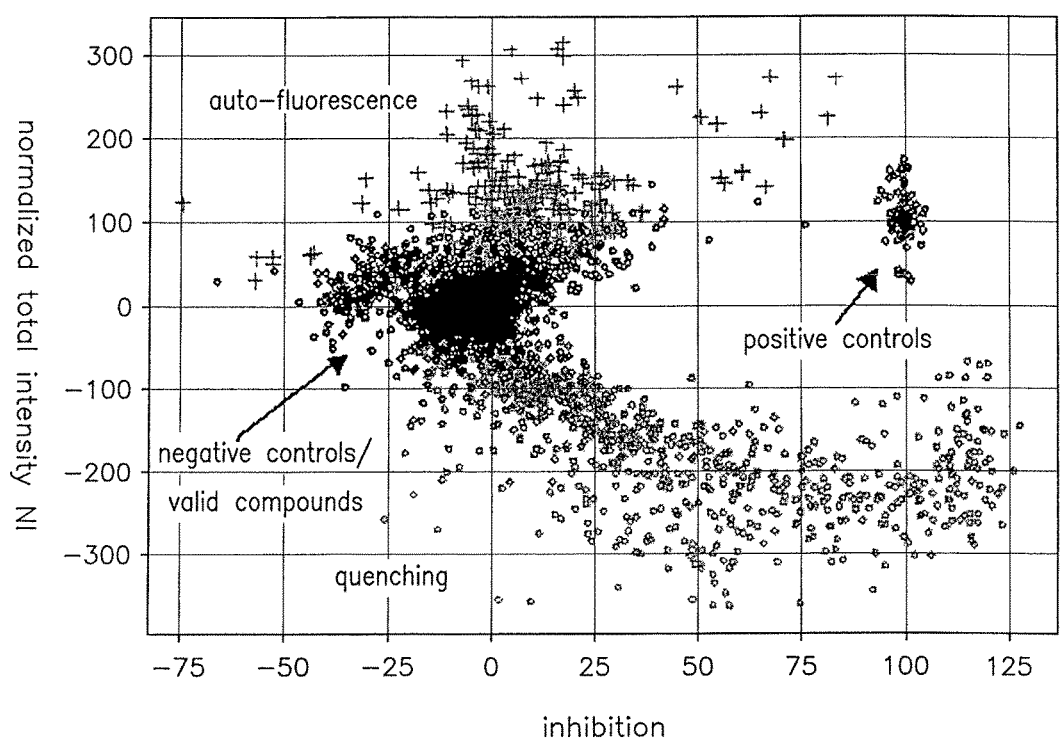

FIGS. 5A-B illustrates an identification of auto-fluorescent and quenching compounds in high-throughput-screening (HTS).

Figure 6:
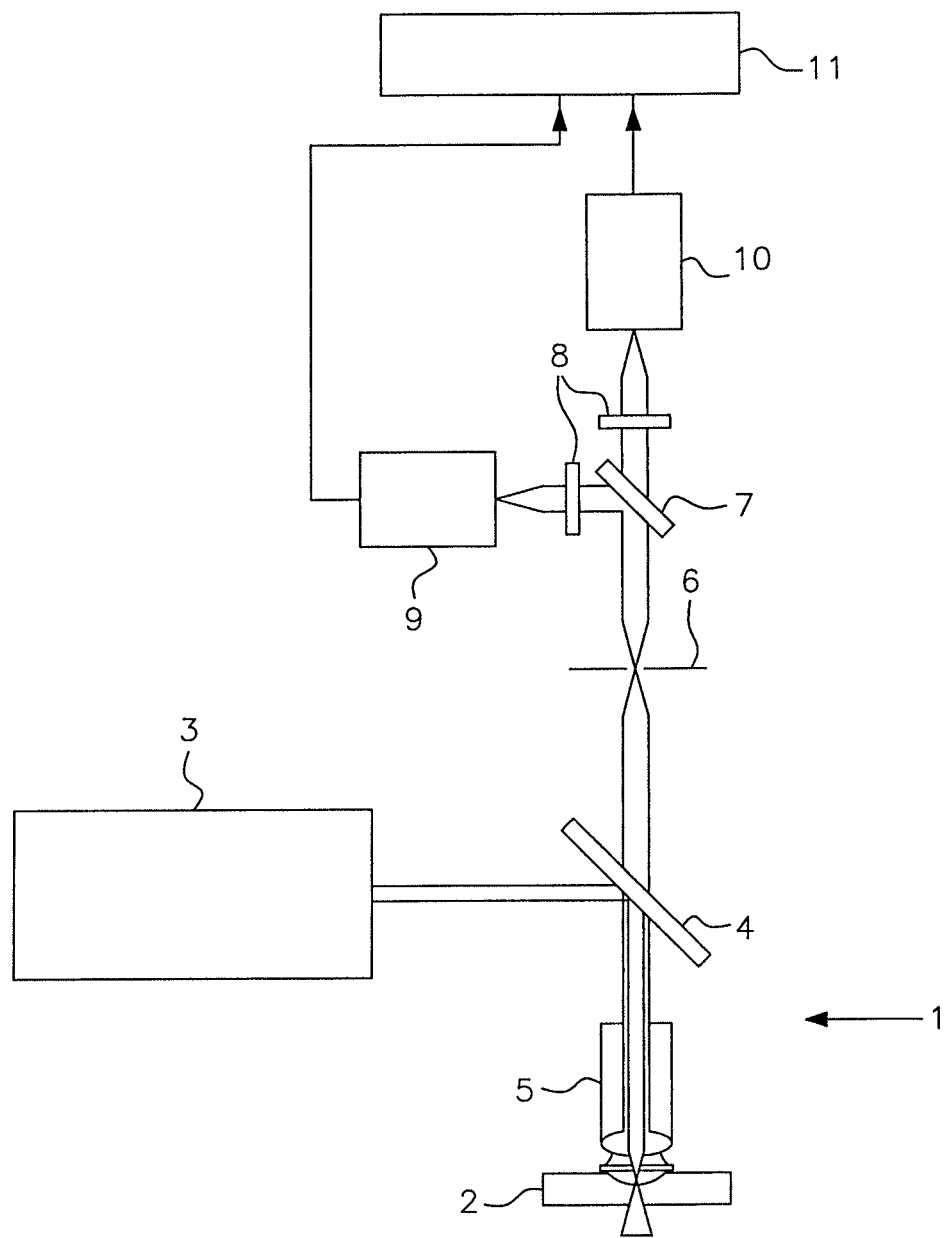

FIG. 6 shows a schematic diagram of a preferred system for detecting the impacts of interfering effects on experimental data resulting from fluorescence measurements.

EXAMPLES

The measurements presented in the following were performed on an epi-illuminated confocal fluorescence microscope as described in [P. Kask, K. Palo, N. Fay, L. Brand, Ü. Mets, D. Ullmann, J. Jungmann, J. Pschorr, K. Gall (2000) Biophys. J, 78, 1703-1713]. A polarized continuous-wave (cw) laser either at 543 nm or 633 nm was used to excite a fluorophore (Tetramethyl-Rhodamine (TAMRA) for 543 nm excitation, MR-121 for 633 nm excitation) alone or covalently linked to a molecule of interest. Detection was performed with a single detector or two detectors (Avalanche-Photo-Diode, APD) monitoring the fluorescence light emitted with parallel or perpendicular polarization with respect to the polarization of the exciting light. While the one-detector set-up was used for the fluorescence data analysis via FIDA, the two-detector set-up was used for the determination of the polarization or anisotropy values and analysis via 2D-FIDA.

Example 1

In a first measurement series, different amounts of various water soluble chemical compounds were added to an aqueous TAMRA solution (about 15 nM, resulting in 96 different samples) and the total intensity, $I_{tot}$, as well as the polarization, P, were determined for the 96 different samples (two-detector set-up and measurement time of two seconds). $I_{tot}$ and P were calculated from the intensities with parallel, $I_P$, and perpendicular, $I_S$, polarization with respect to the exciting light.

$$I_{tot}=I_P+2I_S P=(I_P-I_S)/(I_P+I_S)\times 1000$$

Subsequently, 4 different methods were applied to identify samples with deteriorated signal as presented in FIG. 1.

FIG. 1A shows the one-dimensional distribution of $I_{tot}$ over all 96 samples (dotted line) together with the thresholds (vertical lines) for identification of deteriorated signal. The thresholds were set according to the median, med($I_{tot}$)=1119.9 kHz, and the median like standard deviation, $s^*(I_{tot})$=145.8 kHz, of $I_{tot}$ from all 96 samples ($s^*$ has been described previously); threshold($I_{tot}$)=med($I_{tot}$)±3×$s^*$($I_{tot}$). All samples that exhibited a value of $I_{tot}$ outside these thresholds were identified to be deteriorated, in this case 12 samples.

Figure 1B:
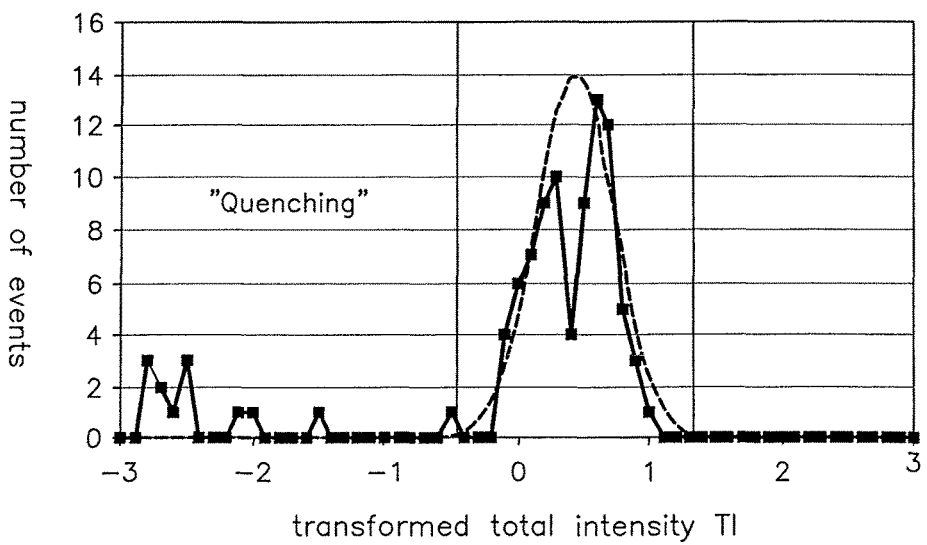

FIG. 1B shows the one-dimensional distribution of the mathematically transformed total intensity, TI, together with a Gaussian fit to the distribution (gray line; $G(TI)=A\times \exp[-(TI-TI_0)^2/(2\sigma^2)]$ with the variables A, $TI_0$, and $\sigma$ subject to fitting and resulting in A=13.9, $TI_0$=0.44, and $\sigma$=0.3) and the thresholds (vertical lines) for identification of deteriorated signal. The mathematical transformation was performed according to the steps; (a) calculation of the median, med($I_{tot}$), of $I_{tot}$ from all 96 samples, (b) calculating the difference, res($I_{tot}$)=$I_{tot}$−med($I_{tot}$), for each sample, (c) determination of the mean, mean(res($I_{tot}$)), and the standard deviation, s(res($I_{tot}$)), of res($I_{tot}$) from all 96 samples, (d) calculating TI=[res($I_{tot}$)−mean(res($I_{tot}$))]/s(res($I_{tot}$)). The thresholds were determined from the resulting value of $\sigma$ and $TI_0$ of the Gaussian fit; threshold(TI)=$TI_0$±3×$\sigma$. All samples that exhibited a value of TI outside these thresholds were identified to be deteriorated, in this case 13 samples.

FIG. 1C shows the one-dimensional distribution of the slightly different mathematically transformed total intensity, TI*, together with a Gaussian fit to the distribution (gray line; $G(TI^*)=A\times\exp[-(TI^*-TI_0^*)^2/(2\sigma^{*2})]$ with the variables A, $TI_0^*$, and $\sigma^*$ subject to fitting and resulting in A=3.788, $TI_0^*$=−0.266, and σ=1.11) and the thresholds (vertical lines) for identification of deteriorated signal. In this case, the mathematical transformation was performed according to the steps; (a) calculation of the median, med$(I_{tot})$, of $I_{tot}$ from all 96 samples, (b) calculating the difference, res$(I_{tot})$=$I_{tot}$−med$(I_{tot})$, for each sample, (c) determination of the median, median(res$(I_{tot})$), and the median like standard deviation, s*(res$(I_{tot})$), of res$(I_{tot})$ from all 96 samples, (d) calculating TI*=[res$(I_{tot})$−median(res$(I_{tot})$)]/s*(res$(I_{tot})$). The thresholds were determined from the resulting value of $\sigma^*$ and $TI_0^*$ of the Gaussian fit; threshold (TI*)=$TI_0^*\pm3\times\sigma^*$. All samples that exhibited a value of TI outside these thresholds were identified to be deteriorated, in this case 12 samples.

FIG. 1D represents the two-dimensional distribution of joint total intensity-polarization pairs, $(I_{tot}, P)$, from all 96 samples (black dots) together with the thresholds (black lines) for identification of deteriorated signal. The thresholds were set according to the median, med$(I_{tot})$=1119.9 kHz and med(P)=30.72, and the median like standard deviation, s*$(I_{tot})$=145.8 kHz and s*(P)=5.15, of $I_{tot}$ and P respectively from all 96 samples; threshold$(I_{tot})$=med$(I_{tot})\pm3\times$s*$(I_{tot})$ and threshold(P)=med(P)±3×s*(P). All samples that exhibited a value of $I_{tot}$ or P outside these thresholds were identified to be deteriorated, in this case 13 samples.

Figure 1E:
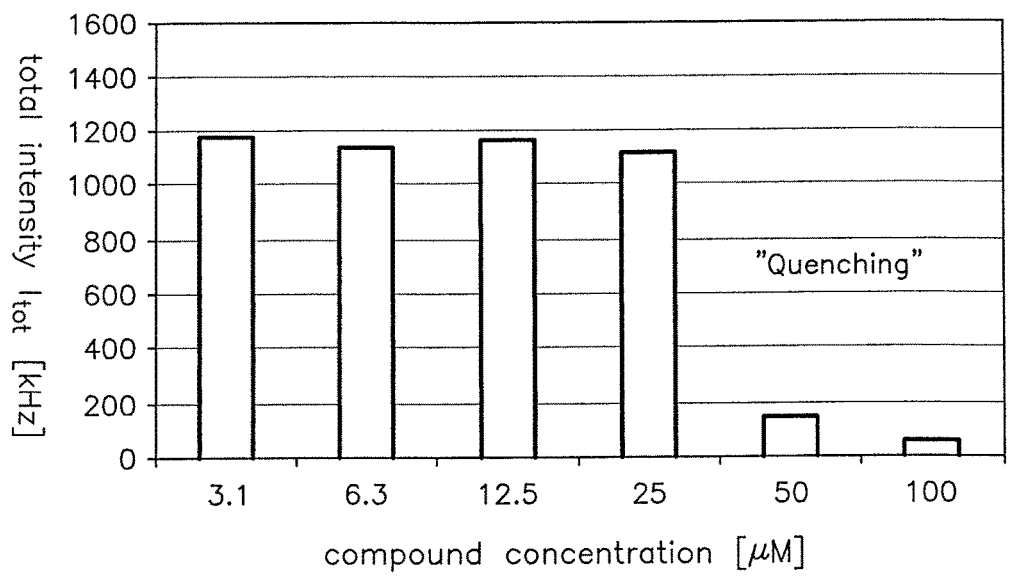
Figure 1F:
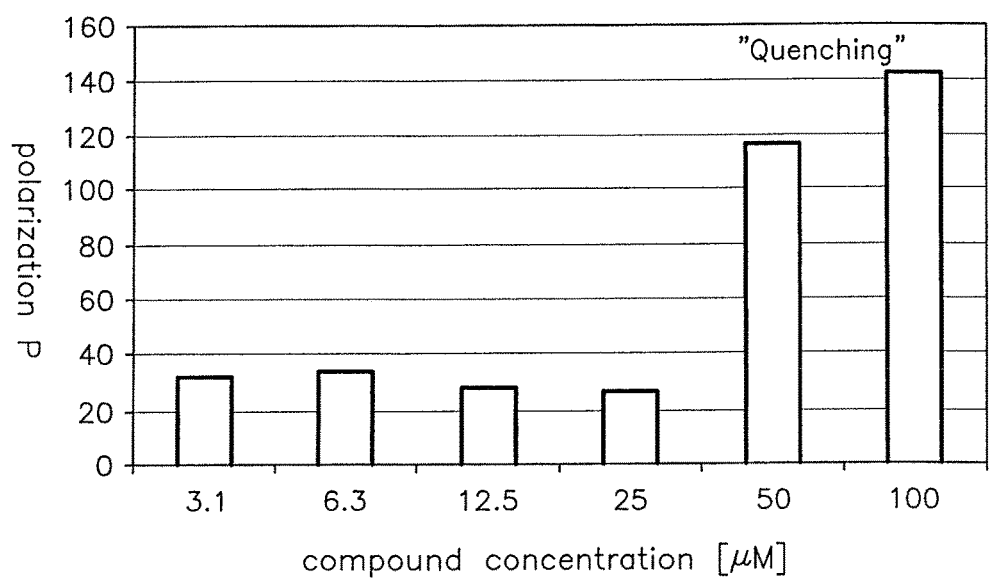

By one or the other method, the same conspicuous samples were identified by a decreased intensity and an increased polarization. To find the reason behind this deterioration, one conspicuous compound was added at rising concentrations to the dye solution. The measured total intensity, $I_{tot}$, and polarization, P, are shown in FIGS. 1E and F, respectively. One clearly observes, that the deterioration was caused by a quenching interference of the compound to the fluorescence emission of the dye, which was a decreasing intensity accompanied by an increase in polarization.

Example 2

In a second measurement series, the binding of a small MR-121-labeled peptide to the SH2-domain of the Grb2-protein was monitored by a change in the fluorescence polarization, P, of the MR-121 fluorescence emission (two-detector set-up, measurement time of ten seconds). In the different samples, the binding was increasingly inhibited by the titration of unlabeled peptide. Thereby, nine different concentrations of unlabeled peptide were measured five times each, i.e. 45 samples were observed. While one set of 45 samples only contained the assay components (labeled and unlabeled peptide and protein), auto-fluorescent compounds (1 μM Rhodamine 800) had been added to another set of 45 samples. 2D-FIDA with a one-component fit was applied to the signal of all samples. This analysis yielded values of concentration, c, brightness, $q_1$ and $q_2$, of each detection channel monitoring the light emission with parallel and perpendicular polarization with respect to the exciting light, respectively, and of chi$^2$, which is the quality parameter of the fit (as presented previously). The total signal intensity was once again calculated from the intensities with parallel, $I_P$, and perpendicular, $I_S$, polarization with respect to the exciting light, while the polarization, P, was calculated from $q_1$ and $q_2$.

$$I_{tot}=I_P+2I_S P=(q_1-q_2)/(q_1+q_2)\times1000$$

In addition, two control samples were measured ten times each, resulting as well in values of c, $q_1$ and $q_2$, chi$^2$, $I_{tot}$, and P. The ten high control samples, which contained only labeled peptide and protein (resulting in mainly bound labeled peptide), resulted in values of c(high), $q_1$(high) and $q_2$(high), chi$^2$(high), $I_{tot}$(high), and P(high). The low control, which contained labeled peptide, excess of unlabeled peptide, and protein (resulting in totally inhibited binding, thus mainly unbound labeled peptide), resulted in values of c(low), $q_1$(low) and $q_2$(low), chi$^2$(low), $I_{tot}$(low), and P(low). This enabled the calculation of the normalized total intensity, NI, and the inhibition, Inh, for each measurement X.

$$NI(X)=[I_{tot}(X)-I_{tot}(\text{low})]/[I_{tot}(\text{high})-I_{tot}(\text{low})]\times100$$

$$Inh(X)=[P(\text{high})-P(X)]/[P(\text{high})-P(\text{low})]\times100$$

Figure 2A:
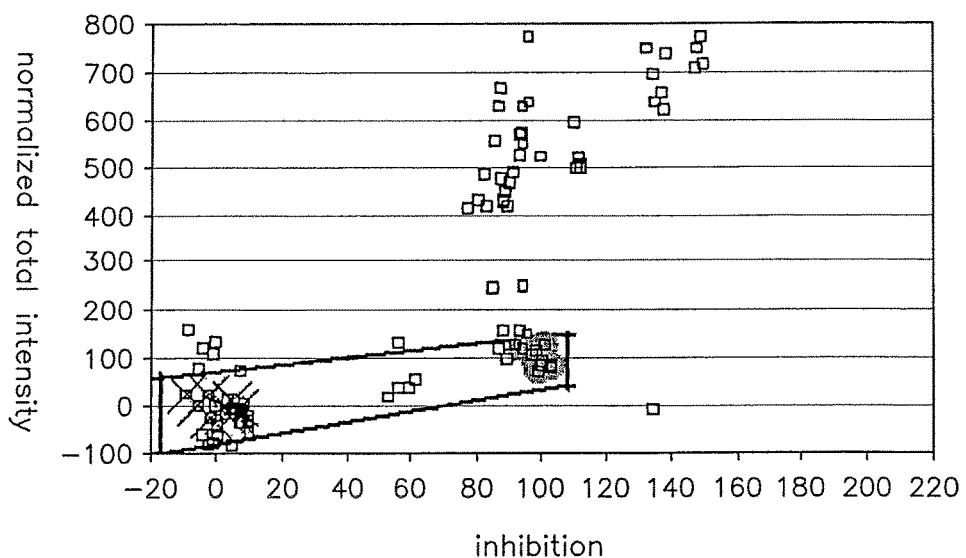

FIGS. 2A and B present two different methods how samples with auto-fluorescence can be identified.

FIG. 2A plots the two-dimensional distribution of joint normalized total intensity-inhibition pairs, (NI, Inh), from both sets of 45 samples (black dots), the high samples (gray cross), and the low samples (gray circles) together with the threshold functions (black lines) for said identification. The thresholds were set by the mean, m(NI,high)=0, m(Inh,high)=0, m(NI,low)=100, and m(Inh,low)=100, and the standard deviation, s(NI,high)=19.7, s(Inh,high)=5.8, s(NI,low)=17.9, and s(Inh,low)=2.7, of NI and Inh from all ten high and low samples, respectively;

t_1(Inh)=m(Inh,high)−3×s(Inh,high),  t_2(Inh)=m(Inh,low)+3×s(Inh,low), t_3(NI)=m(NI,low)−3×s(NI,low),  t_4(NI)=m(NI,low)+3×s(NI,low), t_5(NI)=m(NI,high)−3×s(NI,high), t_6(NI)=m(NI,high)+3×s(NI,high), An auto-fluorescent sample was identified if its read-out, NI or Inh, obeyed one of the following conditions;

Inh<t_1(Inh), Inh>t_2(Inh), NI<$a_1+b_1\times$Inh, or NI>$a_2+b_2\times$Inh, with $a_1$=t_3(NI)−$b_1$×m(Inh,low),   $a_2$=t_4(NI)−$b_2$×m(Inh,low), $b_1$=[t_3(NI)−t_5(NI)]/[m(Inh,low)−m(Inh,high)], and
$b_2$=[t_4(NI)−t_6(NI)]/[m(Inh,low)−m(Inh,high)].

In this way, all 45 samples with added auto-fluorescence were identified.

Figure 2B:
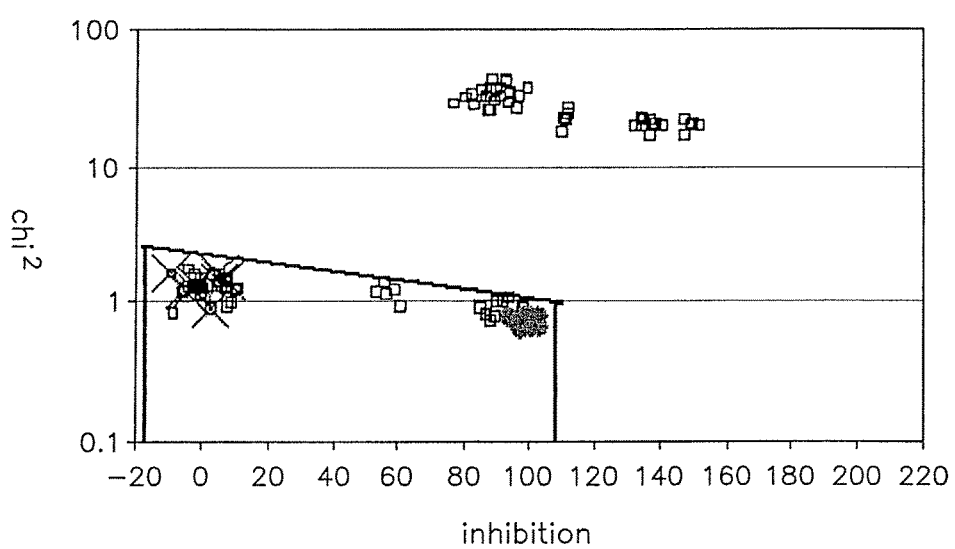

FIG. 2B plots the two-dimensional distribution of chi$^2$-inhibition pairs, (chi$^2$, Inh), from both sets of 45 samples (black dots), the high samples (gray cross), and the low samples (gray circles) together with the threshold functions (black lines) for said identification. The thresholds were set by the mean, m(chi$^2$,high)=1.37, m(Inh,high)=0, m(chi$^2$,low)=0.71, and m(Inh,low)=100, and the standard deviation, s(chi$^2$,high)=0.24, s(Inh,high)=5.8, s(chi$^2$,low)=0.06, and s(Inh,low)=2.7, of chi$^2$ and Inh from all ten high and low samples, respectively;

t_1(Inh)=m(Inh,high)−3×s(Inh,high),  t_2(Inh)=m(Inh,low)+3×s(Inh,low), t_3(chi$^2$)=m(chi$^2$,low)−5×s(chi$^2$,low), t_4(chi$^2$)=m(chi$^2$,low)+5×s(chi$^2$,low), t_5(chi$^2$)=m(chi$^2$,high)−5×s(chi$^2$,high),  t_6(chi$^2$)=m(chi$^2$,high)+5×s(chi$^2$,high), An auto-fluorescent sample was identified if its read-out, $chi^2$ or Inh, obeyed one of the following conditions;

Inh<t_1(Inh), Inh>t_2(Inh), $chi^2$<$a_1+b_1\times$Inh, or $chi^2$>$a_2+b_2\times$Inh, with $a_1$=t_3($chi^2$)–$b_1\times$m(Inh,low), $a_2$=t_4($chi^2$)–$b_2\times$m(Inh, low), $b_1$=[t_3($chi^2$)–t_5($chi^2$)]/[m(Inh,low)–m(Inh,high)], and $b_2$=[t_4($chi^2$)–t_6($chi^2$)]/[m(Inh,low)–m(Inh,high)].

Once again, all 45 samples with added auto-fluorescence were identified.

Figure 2C:
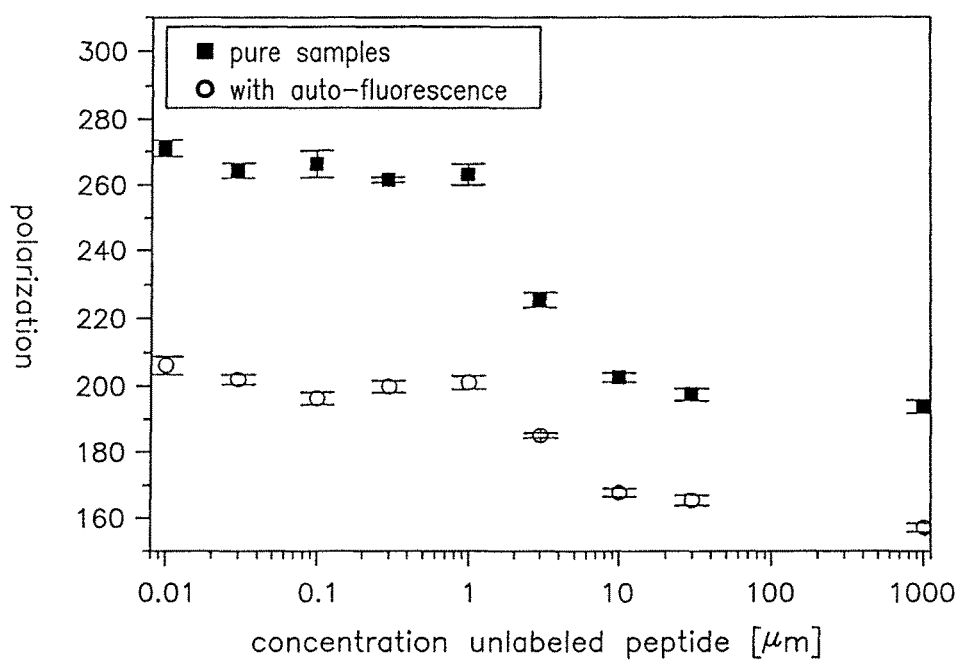
Figure 2D:
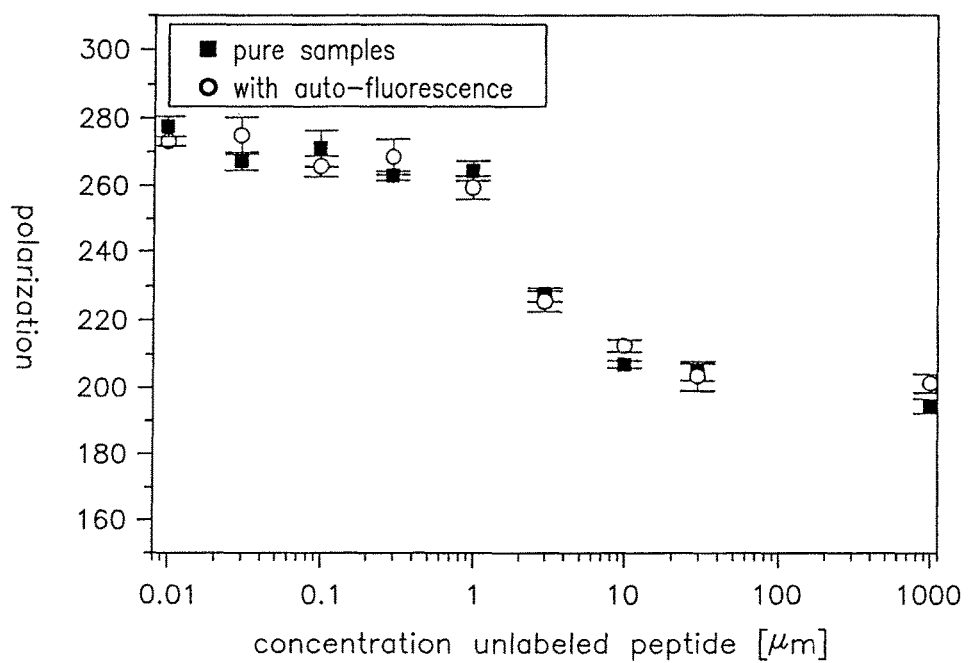

FIG. 2C shows the titration curves for the pure samples (black dots) and the samples with added auto-fluorescence (transparent dots), i.e. the curve shows the change of the polarization, P, with increasingly added unlabeled peptide (the error bars were obtained from the results of the five samples observed for each titration point). The effect of the auto-fluorescence on the detected fluorescence becomes evident by a decreased polarization value. Fitting the auto-fluorescent samples with an additional pair of floating FIDA-background values resulted in a correction of the read-out. This is demonstrated in FIG. 2D, where the corrected read-out of the auto-fluorescent samples coincides with the read-out of the pure samples.

Figure 2E:
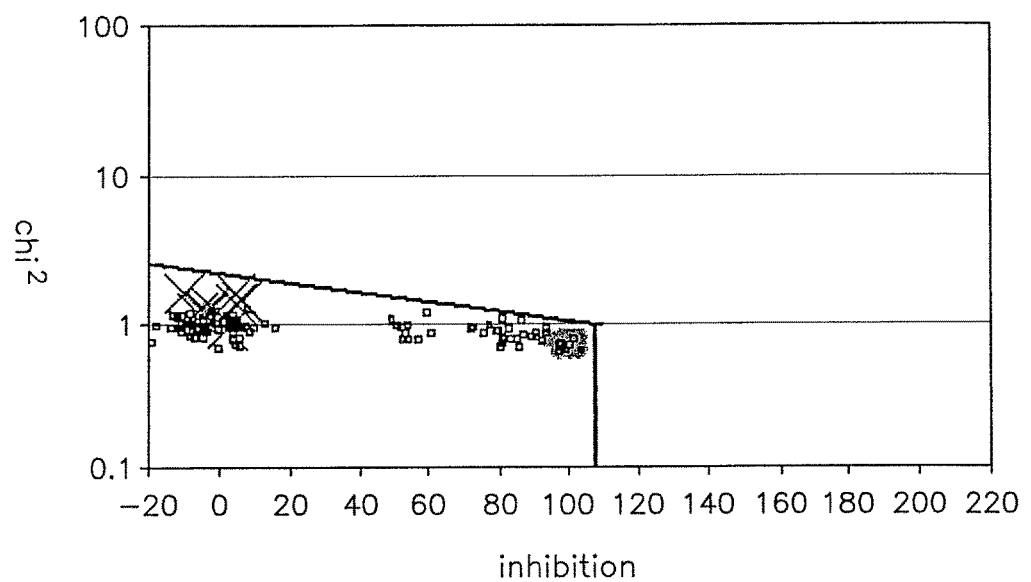

FIG. 2E demonstrates the test procedure of the correction step. Similar to FIG. 2B, it plots the two-dimensional distribution of corrected $chi^2$-inhibition pairs, ($chi^2$, Inh), from both sets of 45 samples (black dots), the low samples (gray cross), and the high samples (gray circles) together with the threshold functions (black lines) for said identification. The thresholds were identically set as in FIG. 2B.

The failure of the correction step was identified if the according read-out, $chi^2$ or Inh, obeyed one of the following conditions;

Inh>t_2(Inh), $chi^2$<$a_1+b_1\times$Inh, or $chi^2$>$a_2+b_2\times$Inh, with $a_1$=t_3($chi^2$)–$b_1\times$m(Inh,low), $a_2$=t_4($chi^2$)–$b_2\times$m(Inh, low), $b_1$=[t_3($chi^2$)–t_5($chi^2$)]/[m(Inh,low)–m(Inh,high)], and $b_2$=[t_4($chi^2$)–t_6($chi^2$)]/[m(Inh,low)–m(Inh,high)].

In this way, only one failure of the correction step was identified.

Example 3

In a third measurement series, the binding of a TAMRA-labeled ligand to membrane vesicles with the appropriate G-protein coupled receptors was monitored using FIDA (one-detector set-up, measurement time of two seconds). The ligand bound to the vesicles can be distinguished from the free ligand by an increase in the fluorescence brightness, q, since the vesicles can bind several ligands. In FIDA, these two components were distinguished in a two-component fit and their brightness, q(ligand) and q(vesicle), and concentration values, c(ligand) and c(vesicle), were determined. For every sample the binding degree was determined according to the equation, binding degree=c(vesicle)×q(vesicle)/[c(vesicle)×q(vesicle)+c(ligand)×q(ligand)].

48 high control and 48 low control sample were measured. The high control contained both, labeled ligand and vesicles, while the low control solely contained labeled ligand. In a first set of measurements, the pure 96 samples were observed. In additional sets of measurement, the 96 samples were observed after adding different amounts of auto-fluorescent substances (0.05 µM, 0.5 µM, and 1 µM of the dye C682). The binding degree resulting from the two-component FIDA fit is shown in FIG. 3A. The apparently decreased binding degree shows the effect of the increasingly added auto-fluorescent substances.

For the correction, a three-component FIDA analysis was performed on the same fluorescence data sets. Thereby, an additional component with floating concentration, c(auto-fluorescence), and fixed brightness value, q(auto-fluorescence)=1 kHz, was added to the two-component fit of FIG. 3A. The fixed brightness value was rather low compared to the mean brightness values obtained for the free ligand, q(ligand)=9 kHz, and the ligand bound to the vesicle, q(vesicle)=1350 kHz. The resulting values of the binding degree coincides with that of the pure samples, which indicates the success of the correction procedure. However, a decreased accuracy of the determination of the binding degree becomes evident by the increased error bars, which is due to the presence of the interfering auto-fluorescence as well as the correction procedure. Therefore, it is recommendable to apply this correction step solely to those samples which are identified to emit auto-fluorescence.

Example 4

In a fourth measurement series, 96 different compounds were tested for the activation of a DNA-binding protein. Upon activation, the protein was able to bind the single DNA strand. Since the DNA strand was labeled with TAMRA, the activation was accompanied by an increase in the polarization, P. A positive compound, which activated the protein, should therefore result in an increase of polarization, P. To check the reactivity of the compounds, the polarization read-out was compared to that of positive and negative controls. While the negative control just like a non-activating compound comprised the unbound DNA strand (low polarization), the positive control just like an activating compound comprised the DNA-peptide complex (high polarization). As in the previous example 2, the measurements were performed with two detectors monitoring the different polarization directions of the light emission and analyzed using 2D-FIDA regarding only one fluorescent component. This resulted in values of the intensity, $I_P$ and $I_S$, as well as of the brightness, $q_1$ and $q_2$, of the fluorescence with parallel and perpendicular polarization with respect to the polarization of the exciting light, respectively, and of the mean concentration, c, of the fluorescent component. This enabled the calculation of the total intensity, $I_{tot}$, the total brightness, $q_{tot}$, the activation, Act, as well as the normalized total signal, NI.

$$I_{tot}=I_P+2I_S q_{tot}=q_1+q_2 P=(q_1-q_2)/(q_1+q_2)\times 1000$$

$$NI(X)=[I_{tot}(X)-I_{tot}(\text{pos})]/[I_{tot}(\text{neg})-I_{tot}(\text{pos})]\times 100$$

$$Act(X)=[P(X)-P(\text{neg})]/[P(\text{pos})-P(\text{neg})]\times 100$$

The whole experiment included the measurement (two second duration) of 96 different compounds added to the assay (labeled DNA and protein) as well as nine positive controls and 96 negative controls.

For the identification of possible auto-fluorescent or quenching compounds, FIG. 4A plots the two-dimensional distribution of joint normalized total intensity-activation pairs, (NI, Act), from the 96 compound samples (black dots), the 96 negative control samples (gray cross), and the six positive control samples (gray circles) together with the threshold functions (black lines) for said identification. In the same way as in FIG. 2A, the thresholds were set by the mean, m(NI,pos)=0, m(Act,pos)=100, m(NI,neg)=100, and m(Act,neg)=0, and the standard deviation, s(NI,pos)=4.1, s(Act,pos)=4.7, s(NI,neg)=9.3, and s(Act,neg)=6.2, of NI and Act from all six positive and 96 negative control samples, respectively;

t_1(Act)=m(Act,neg)−3×s(Act,neg), t_2(Act)=m(Act, pos)+3×s(Act,pos), t_3(NI)=m(NI,neg)−3×s(NI,neg), t_4(NI)=m(NI,neg)+3× s(NI,neg), t_5(NI)=m(NI,pos)−3×s(NI,pos), t_6(NI)=m(NI,pos)+3× s(NI,pos).

An auto-fluorescent compound sample was identified if its read-out, NI or Act, was above the upper threshold line, i.e. obeyed the following condition;

$$NI > a_2 + b_2 \times Act,$$

with $a_2 = t\_4(NI) - b_2 \times m(Act,neg)$, and
$b_2 = [t\_4(NI) - t\_6(NI)]/[m(Act,neg) - m(Act,pos)]$.

In this way, 67 compound samples were identified to be auto-fluorescent.

A quenching compound sample was identified if its read-out, NI or Act, was below the lower threshold line or elsewhere to the left or right of the two vertical lines, i.e. obeyed one of the following conditions and was not auto-fluorescent;

$$Act < t\_1(Act), Act > t\_2(Act), \text{ or } NI < a_1 + b_1 \times Act,$$

with $a_1 = t\_3(NI) - b_1 \times m(Act,neg)$, and,
$b_1 = [t\_3(NI) - t\_5(NI)]/[m(Act,neg) - m(Act,pos)]$.

In this way, two compound samples were identified to be quenching and taken away from further analysis (bad data points).

In a second step, the correction procedure was applied to the fluorescence data from the compound samples identified as being auto-fluorescent (while the results of the analysis were maintained for the valid compound samples). The correction procedure comprised a 2D-FIDA fit regarding one component as before and in addition two floating FIDA-background values as already applied in example 2. The success of the correction procedure was checked (see FIG. 4B). Similar to FIG. 2B, it plots the two-dimensional distribution of the corrected total brightness-activation pairs, ($q_{tot}$, Act), from the 94 left samples (black dots), the 96 negative samples (gray cross), and the six positive samples (gray circles) together with the threshold functions (black lines) for the identification of failures of the correction algorithm or the analysis in principle. The thresholds were set by the mean, m($q_{tot}$,pos)=68.0, m(Act,pos)=100, m($q_{tot}$,neg)=58.4, and m(Act,neg)=0, and the standard deviation, s($q_{tot}$,pos)=3.7, s(Act,pos)=4.7, s($q_{tot}$,neg)=3.5, and s(Act,neg)=6.2, of $q_{tot}$ and Act from all six positive and 96 negative control samples, respectively;

t_1(Act)=m(Act,neg)−3×s(Act,neg), t_2(Act)=m(Act, pos)+3×s(Act,pos), t_3($q_{tot}$)=m($q_{tot}$,neg)−5×s($q_{tot}$,neg), t_4($q_{tot}$)=m($q_{tot}$, neg)+5×s($q_{tot}$,neg), t_5($q_{tot}$)=m($q_{tot}$,pos)−5×s($q_{tot}$,pos), t_6($q_{tot}$)=m($q_{tot}$, pos)+5×s($q_{tot}$,pos).

The said failure was identified if the according read-out, $q_{tot}$ or Act, obeyed one of the following conditions;

$$Act > t\_2(Act), q_{tot} < a_1 + b_1 \times Act, \text{ or } q_{tot} > a_2 + b_2 \times Act,$$

with $a_1 = t\_3(q_{tot}) - b_1 \times m(Act,low)$, $a_2 = t\_4(q_{tot}) - b_2 \times m(Act, low)$,
$b_1 = [t\_3(q_{tot}) - t\_5(chi^2)]/[m(Act,low) - m(Act,high)]$, and
$b_2 = [t\_4(q_{tot}) - t\_6(q_{tot})]/[m(Act,low) - m(Act,high)]$.

In this way, eight failures of the whole analysis process were identified.

Using the identification step and correction procedure, together with the failure check, one can not only exclude possible false positive compounds (i.e., apparently activating in this case) due to auto-fluorescence or quenching, but also correct the read-out for auto-fluorescent compounds. In a drug discovery process, this does not only save precious money and time, but also helps to find possible positive and auto-fluorescent drug candidates which would otherwise be lost.

Example 5

In a further measurement series, the identification step was applied to a high-throughput-screening (HTS) run. In this HTS run different compounds were tested for the inhibition of the dephosphorylation of a phosphotyrosine-containing peptide by an appropriate protein tyrosine phosphatase. An antibody was used in this experiment which only binds to the phosphorylated peptide. Since the peptide was fluorescently labeled, binding of the antibody to the phosphorylated peptide increased the polarization, P, of this complex. Therefore, dephosphorylation resulted in a loss of antibody binding and concomitant decrease of polarization. A positive compound, which inhibited the dephosphorylation, should therefore result in an increase of polarization, P. To check the reactivity of the compounds, the polarization read-out was compared to that of positive and negative controls. While the negative control just like a non-inhibiting compound comprised the dephosphorylated peptide (low polarization), the positive control just like an inhibiting compound comprised the antibody-peptide complex (high polarization). As in the previous examples 2 and 4, the measurements were performed with two detectors monitoring the different polarization directions of the light emission and analyzed using 2D-FIDA with a one-component fit. As outlined, this enabled the calculation of the inhibition, Inh, as well as the normalized total signal, NI.

6144 different compounds were added to the assay (labeled peptide, antibody, and phosphatase) and distributed on four different nanotiter-plates with 2080 wells each. Furthermore, each plate contained 24 positive and 24 negative control samples. The HTS run was performed by measuring each sample once for one second. The identification step for auto-fluorescent or quenching compounds is outlined in FIG. 5A. In the same way as outlined in detail in FIG. 2A and FIG. 4A, the threshold conditions for the identification were set individually for each plate according to the mean values and standard deviations of Inh and NI of the positive and negative controls (mean±3×standard deviation).

This is shown in FIG. 5A for one of the four plates, where the threshold lines (black lines) are drawn such as in FIGS. 2A and 4A. The compound samples exhibiting a read-out pair of (Inh,NI) above the upper line were classified as auto-fluorescent compounds (gray cross), while compound samples exhibiting a read-out pair of (Inh,NI) below the lower line were classified as quenching compounds (gray circles). Valid compound samples as well as positive and negative controls (black circles) lie in between the threshold lines. In this way, 1313 compounds were classified to be valid, 166 (10.8%) to be quenching, and 57 (3.7%) to be auto-fluorescent.

FIG. 5B plots the pairs (Inh, NI) from all four plates. The identification step was performed for each plate independently. In this way, 4966 valid (black circles), 819 quenching (13.3%, gray circles), and 365 auto-fluorescent compounds (5.9%, gray cross) were identified in this HTS run.

Since the inhibition values obtained from the samples with auto-fluorescent and quenching compounds in a lot of cases pretend a positive inhibiting property of the according compound (compare FIG. 5), this identification step avoids the detection of false positives and helps to save precious money and time in the drug discovery process when using HTS.

Example 6

FIG. 6 shows a schematic diagram of a preferred system for detecting the impacts of interfering effects on experimental data resulting from fluorescence measurements. Preferably, the fluorescence measurements are performed with a confocal epi-illuminated microscope.

Means in an inspection station (2) support one or a plurality of samples (e.g. a moveable microscope table with a 4×6-, 96-, 384-, 1536-, or 2080-well glass bottom well plate, the wells being filled with the samples). Preferably, the samples comprise dye-labeled molecules at a rather low concentration below 20 nM. Furthermore, the inspection station can preferably be moved with respect to the rest of the system.

One or a plurality of light sources (3) serve for the excitation of fluorescence emission within the sample. Preferably, the light sources are linearly polarized lasers at wavelengths between 350 and 700 nm, which are either continuous wave or pulsed in the case of fluorescence lifetime measurements. In order to guide the excitation light onto the sample, it is reflected by a mirror (4) and focused into the sample by a lens (5). Preferably, the mirror is dichroitic, i.e. it reflects the excitation light and transmits the fluorescence light. Preferably, the lens is an objective lens, which focuses the light to an almost diffraction limited spot of about 1 μm diameter, thereby causing fluorescence emission within the sample.

For the detection of the fluorescence emission, the system comprises an optical set-up which directs the fluorescence on at least one of the detectors (9, 10). The fluorescence of the sample is collected by the same lens (5), transmits the mirror (4), and is focused onto a pinhole (6). The pinhole, which preferably has a diameter of 10 to 200 μm, blocks out-of-focus light and transmits only fluorescence light, which is emitted within the focal part of the excitation light, i.e. a volume of about fL-size. After the pinhole, the fluorescence is guided to one or more detectors (9, 10). It can be split into several components by one or more mirrors (7), which preferably split the fluorescence into its components of different polarization and/or color. Before impinging onto the detectors, the fluorescence radiation can pass optical filters (8), which preferably transmit the fluorescence and block unwanted radiation such as scattering from the solvent. Preferably, the detectors (9, 10) are avalanche photodiodes, which convert the impinged fluorescence radiation into an electrical signal with a very high efficiency.

A signal processing unit (11) converts the electrical signal of the one or the plurality of detectors into experimental data, which is preferably a stream of fluorescence photon counts. In further processing steps, the unit (11) determines the values of one or a plurality of identification parameters from the experimental data, which is e.g. the amount of detected fluorescence—e.g. the fluorescence intensity, the number of counts and/or the count-rate—, a ratio of fluorescence intensities at selected wavelengths, a ratio of fluorescence intensities at different polarization directions, a fluorescence anisotropy, a fluorescence polarization, a fluorescence lifetime, a rotational correlation time, a diffusion constant, a concentration of fluorophores, a specific fluorescence brightness, and/or a function of these. For this determination, the signal processing unit uses preferably analysis techniques such as FCS, 1D- and/or 2D-FIDA, FILDA, fluorescence lifetime and/or time-resolves anisotropy analysis, and/or FIMDA. Furthermore, the signal processing unit (11) might coordinate the movement of the sample support within the inspection station. The signal processing unit preferably contains a storage unit, which stores the determined values of identification parameters in relation to the respective position of the sample support. The signal processing unit (11) as well creates an histogram or distribution of the values of the identification parameters and determines thresholds for the values of the identification parameters, which thresholds are indicative for the impact of interfering effects. It analyzes the values of the identification parameters for the different positions of the sample support within the inspection station and determines whether or not these values fulfill criteria with respect to the thresholds. It also supplies as output information those data which are influenced and/or not influenced by the interfering effects. Furthermore, the unit (11) includes means for correcting the data for the impact of the interfering effect and means for the conductance of a control step to check the success of the correction.

The invention claimed is:

1. A system for detecting the impact of and correcting for interfering effects of auto-fluorescence, fluorescence quenching, and fluorescence-signal deterioration on fluorescence emission data resulting from fluorescence measurements, said system comprising:
   (i) a device for supporting one or a plurality of samples selected from the group consisting of drug-candidate samples and patient-specimen samples in an inspection station,
   (ii) one or a plurality of fluorescence signal detectors which are positioned relative to the inspection station so that a fluorescence signal emitted from the samples impinges on the fluorescence signal detectors, and
   (iii) a fluorescence signal processing unit programmed to perform the steps of
      receiving fluorescence emission data generated by the fluorescence signal detectors,
      determining values of a plurality of fluorescence identification parameters from said fluorescence emission data including at least first and second corresponding fluorescence identification parameters,
      storing the determined values in such a manner that all the determined values which relate to any one of the samples are linked,
      creating a multi-dimensional histogram or distribution of the determined values of the fluorescence identification parameters,
      determining thresholds for the determined values of the fluorescence identification parameters from said multi-dimensional histogram or distribution, which thresholds are indicative of interfering effects selected from the group consisting of auto-fluorescence, fluorescence quenching, and fluorescence-signal deterioration, wherein the threshold for the determined values of the first fluorescence identification parameter is a function of the corresponding second fluorescence identification parameter, analyzing the determined values of the plurality of fluorescence identification parameters whether or not the determined values fulfill one or a plurality of criteria with respect to the thresholds, supplying as output information fluorescence emission data influenced by the interfering effects, fluorescence emission data not affected by the interfering effects, or fluorescence emission data influenced by the interfering effects and fluorescence emission data not affected by the interfering effects, and using the output information to detect at least one of false positive drug-candidate test results in the fluorescence emission data, false negative drug-candidate test results in the fluorescence emission data, false positive diagnostic test results in the fluorescence emission data, and false negative diagnostic test results in the fluorescence emission data.

2. The system of claim 1 further comprising a fluorescence reader.

3. The system of claim 1 further comprising a fluorescence reader including a confocal optical set-up.

4. The system of claim 1 wherein the photosensitive detector comprises an avalanche photodiode or a charged coupled device (CCD) camera.

\* \* \* \* \*